US010441411B2

(12) United States Patent
Sohn et al.

(10) Patent No.: US 10,441,411 B2
(45) Date of Patent: Oct. 15, 2019

(54) ACCOMMODATIVE INTRAOCULAR LENS

(71) Applicant: RAINBOW MEDICAL LTD., Herzliya (IL)

(72) Inventors: Zev Sohn, Ginot Shomron (IL); Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 151 days.

(21) Appl. No.: 15/393,947

(22) Filed: Dec. 29, 2016

(65) Prior Publication Data

US 2018/0185139 A1    Jul. 5, 2018

(51) Int. Cl.
*A61F 2/16*    (2006.01)

(52) U.S. Cl.
CPC .......... *A61F 2/1648* (2013.01); *A61F 2/1629* (2013.01); *A61F 2/1632* (2013.01); *A61F 2002/1682* (2015.04); *A61F 2002/16902* (2015.04)

(58) Field of Classification Search
None
See application file for complete search history.

(56) References Cited

U.S. PATENT DOCUMENTS

| | | |
|---|---|---|
| 4,704,125 A | 11/1987 | Ruminson |
| 4,711,638 A | 12/1987 | Lindstrom |
| 4,778,463 A | 10/1988 | Hetland |
| 4,863,465 A | 9/1989 | Kelman |
| 4,950,289 A | 8/1990 | Krasner |
| 5,275,623 A | 1/1994 | Sarfarazi |
| 5,824,074 A | 10/1998 | Koch |
| 5,968,094 A | 10/1999 | Werblin et al. |
| 6,013,101 A | 1/2000 | Israel |

(Continued)

FOREIGN PATENT DOCUMENTS

| | | |
|---|---|---|
| CN | 201015617 Y | 2/2008 |
| WO | 2009/021326 A1 | 2/2009 |

(Continued)

OTHER PUBLICATIONS

Communication dated Jan. 8, 2018 from the United States Patent and Trademark Office in counterpart U.S. Appl. No. 15/170,417.

(Continued)

*Primary Examiner* — Leslie Lopez
(74) *Attorney, Agent, or Firm* — Sughrue Mion, PLLC

(57) ABSTRACT

An accommodating intraocular lens implant is provided that is shaped so as to be assemblable into an assembled state in situ in a capsular bag of a human eye, and includes an anterior floating lens unit, which comprises an anterior lens; a posterior lens unit, which comprises a posterior lens; an anterior rim; levers, arranged to move the anterior floating lens unit toward and away from the anterior rim, in an anterior-posterior direction; and a circumferential rim, which is attached to the levers. The lens implant is arranged such that in the assemble state: elastic potential energy is stored in the lens implant as a result of deformation of the lens implant during a transition from a fully-accommodated state to a fully-unaccommodated state, and at least 50% of the elastic potential energy stored in the lens implant as the result of the deformation is stored in the circumferential rim.

35 Claims, 15 Drawing Sheets

(56) References Cited

U.S. PATENT DOCUMENTS

| | | | |
|---|---|---|---|
| 6,117,171 | A | 9/2000 | Skottun |
| 6,231,603 | B1 | 5/2001 | Lang et al. |
| 6,423,094 | B1 | 7/2002 | Sarfarazi |
| 6,464,725 | B2 | 10/2002 | Skottun |
| 6,488,708 | B2 | 12/2002 | Sarfarazi |
| 6,524,340 | B2 | 2/2003 | Israel |
| 6,660,035 | B1 | 12/2003 | Lang et al. |
| 6,767,363 | B1 | 7/2004 | Bandhauer et al. |
| 6,884,263 | B2 | 4/2005 | Valyunin et al. |
| 7,223,288 | B2 | 5/2007 | Zhang et al. |
| 7,238,201 | B2 | 7/2007 | Portney et al. |
| 7,416,562 | B2 | 8/2008 | Gross |
| 7,871,437 | B2 | 1/2011 | Hermans et al. |
| 2002/0107568 | A1 | 8/2002 | Zadno-Azizi et al. |
| 2002/0111678 | A1 | 8/2002 | Zadno-Azizi et al. |
| 2003/0109925 | A1 | 6/2003 | Ghazizadeh et al. |
| 2003/0204255 | A1 | 10/2003 | Peng et al. |
| 2004/0082993 | A1 | 4/2004 | Woods |
| 2004/0148023 | A1 | 7/2004 | Shu |
| 2006/0001186 | A1 | 1/2006 | Richardson et al. |
| 2007/0156236 | A1 | 7/2007 | Stenger |
| 2008/0051886 | A1 | 2/2008 | Lin |
| 2008/0097461 | A1 | 4/2008 | Boukhny et al. |
| 2009/0228101 | A1 | 9/2009 | Zadno-Azizi |
| 2011/0071628 | A1 | 3/2011 | Gross et al. |
| 2011/0295368 | A1 | 12/2011 | Betser |
| 2013/0184816 | A1 | 7/2013 | Hayes |
| 2013/0197636 | A1 | 8/2013 | Haefliger |
| 2014/0052246 | A1 | 2/2014 | Kahook et al. |
| 2014/0180407 | A1 | 6/2014 | Sohn et al. |
| 2014/0309734 | A1 | 10/2014 | Sohn et al. |
| 2014/0309735 | A1* | 10/2014 | Sohn ..................... A61F 2/1648 623/6.34 |
| 2016/0015648 | A1 | 1/2016 | Gross et al. |

FOREIGN PATENT DOCUMENTS

| | | | |
|---|---|---|---|
| WO | 2009/021327 | A1 | 2/2009 |
| WO | 2010/089689 | | 8/2010 |
| WO | 2013/016804 | A1 | 2/2013 |
| WO | 2013/126986 | A1 | 9/2013 |
| WO | 2015/198236 | | 12/2015 |
| WO | 2016/161519 | A1 | 10/2016 |
| WO | 2017/181295 | A1 | 10/2017 |
| WO | 2017/208230 | A1 | 12/2017 |

OTHER PUBLICATIONS

Communication dated Jan. 29, 2018 from the United States Patent and Trademark Office in counterpart U.S. Appl. No. 15/125,916.
Communication dated Jan. 4, 2018 from the European Patent Office in counterpart application No. 15811584.0.
International Search Report and Written Opinion dated Aug. 30, 2017 issued by the International Searching Authority in corresponding application No. PCT/IL2017/050594.
International Search Report and Written Opinion dated Feb. 26, 2018 issued by the International Searching Authority in corresponding application No. PCT/IL2017/051317.
Invitation to Pay Additional Fees dated Oct. 9, 2015, which issued during the prosecution of Applicant's PCT/IB2015/054730.
International Search Report and Written Opinion in PCT/IB2015/054730, dated Dec. 28, 2015.
An Office Action dated Feb. 2, 2015, which issued during the prosecution of U.S. Appl. No. 14/139,579.
McLeod SD et al., "Synchrony dual-optic accommodating intraocular lens Part 1: Optical and biomechanical principles and design considerations," J Cataract Refract Surg. 2007; 33:37-46.
Ossma IL et al., "Synchrony Dual-Optic Accommodating Intraocular Lens Part 2: Pilot Clinical Evaluation," J Cataract Refract Surg. 2007; 33:47-52.
Crystalens 5.0 (Model AT-50SE), Mar. 2007.
Crystalens, Don't just see. See better, pp. 1-3, Sep. 2009.
U.S. Appl. No. 61/150,762, filed Feb. 8, 2009.
An International Search Report dated Jun. 18, 2010, which issued during the prosecution of Applicant's PCT/IB2010/050421.
StabilEyes® Capsular Tension Ring, Abbott Medical Optics, http://www.amo-inc.com/products/cataract/supportsystems/stabileyes-capsular-tension-ring, downloaded Mar. 9, 2014.
An Office Action dated Aug. 2, 2011, which issued during the prosecution of U.S. Appl. No. 12/566,029.
An Office Action dated May 5, 2011, which issued during the prosecution of U.S. Appl. No. 12/566,029.
An Office Action dated Jan. 27, 2012, which issued during the prosecution of U.S. Appl. No. 12/566,029.
An Office Action dated Jul. 15, 2015, which issued during the prosecution of U.S. Appl. No. 14/315,301.
An Office Action dated May 26, 2016, which issued during the prosecution of U.S. Appl. No. 14/315,301.
An Office Action dated Oct. 30, 2015, which issued during the prosecution of U.S. Appl. No. 14/315,301.
An Office Action dated Nov. 5, 2014, which issued during the prosecution of U.S. Appl. No. 14/139,579.
Still image excerpts from Modular IOL Video, ClarVista Medical, posted to YouTube.com on Dec. 5, 2013 (https://www.youtube.com/watch?v=-dAAPFH0qRQ).
TECNIS® 3-Piece IOL, Abbott Medical Optics, http://www.amo-inc.com/products/cataract/monofocal-iols/tecnisaspheric-iol, downloaded Mar. 9, 2014.
Krader CG, "Modular IOL system begins clinical evaluation," Ophthalmology Times, Jan. 2014.
Interview Summary Report dated Feb. 18, 2016, which issued during the prosecution of U.S. Appl. No. 14/315,301.
Interview Summary Report dated Jun. 14, 2016, which issued during the prosecution of U.S. Appl. No. 14/315,301.
An Interview Summary dated Jul. 6, 2017, which issued during the prosecution of U.S. Appl. No. 14/315,301.
An Interview Summary dated Jan. 10, 2017, which issued during the prosecution of U.S. Appl. No. 14/315,301.
An Office Action dated May 5, 2017, which issued during the prosecution of U.S. Appl. No. 14/315,301.
An Advisory Action dated Oct. 27, 2016, which issued during the prosecution of U.S. Appl. No. 14/315,301.
Communication dated Jun. 28, 2018 from the United States Patent and Trademark Office in counterpart U.S. Appl. No. 15/125,916.
Communication dated Aug. 7, 2018 from the United States Patent and Trademark Office in counterpart U.S. Appl. No. 15/170,417.
Communication dated Nov. 16, 2018 from the United States Patent and Trademark Office in counterpart U.S. Appl. No. 15/125,916.

\* cited by examiner

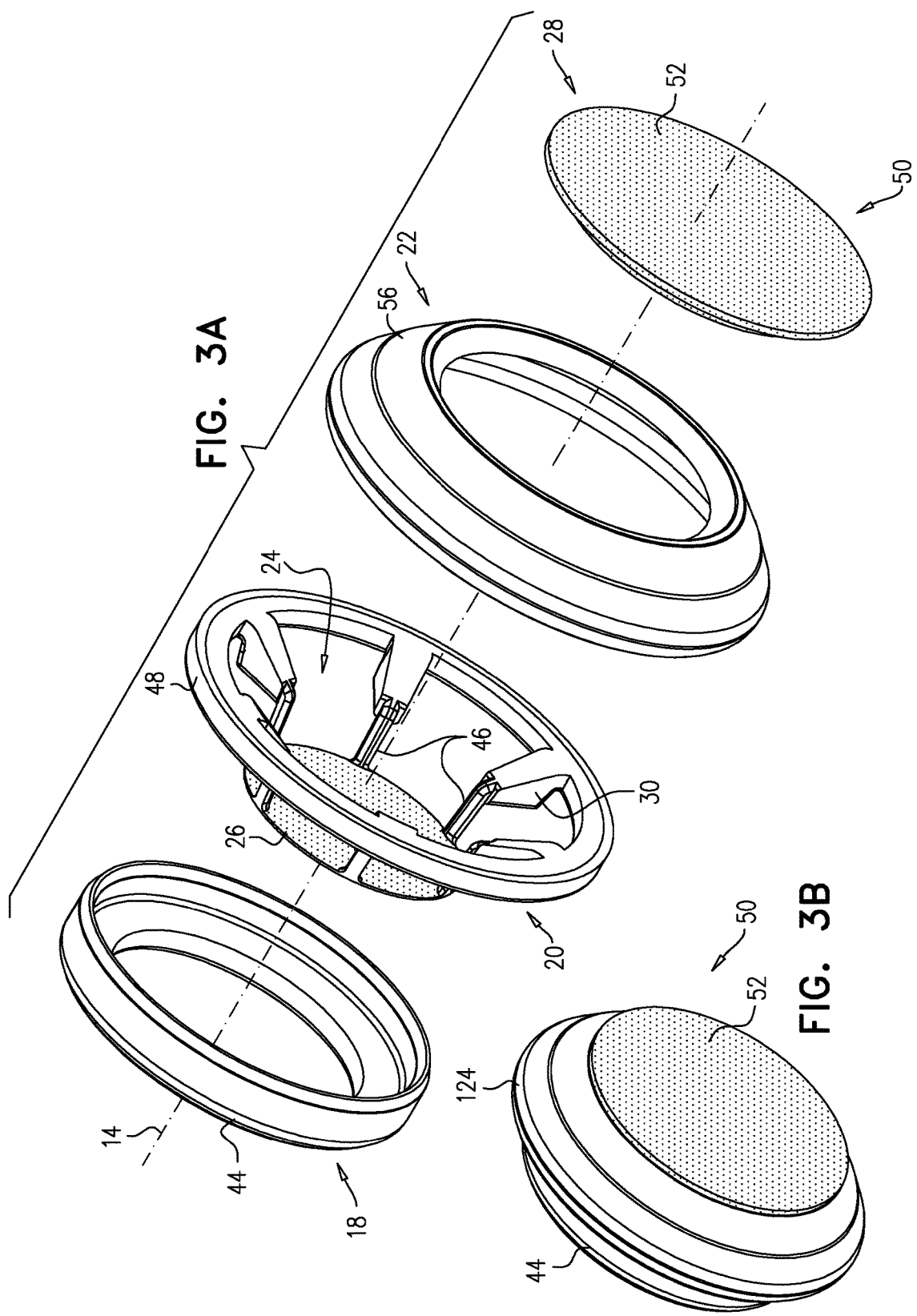

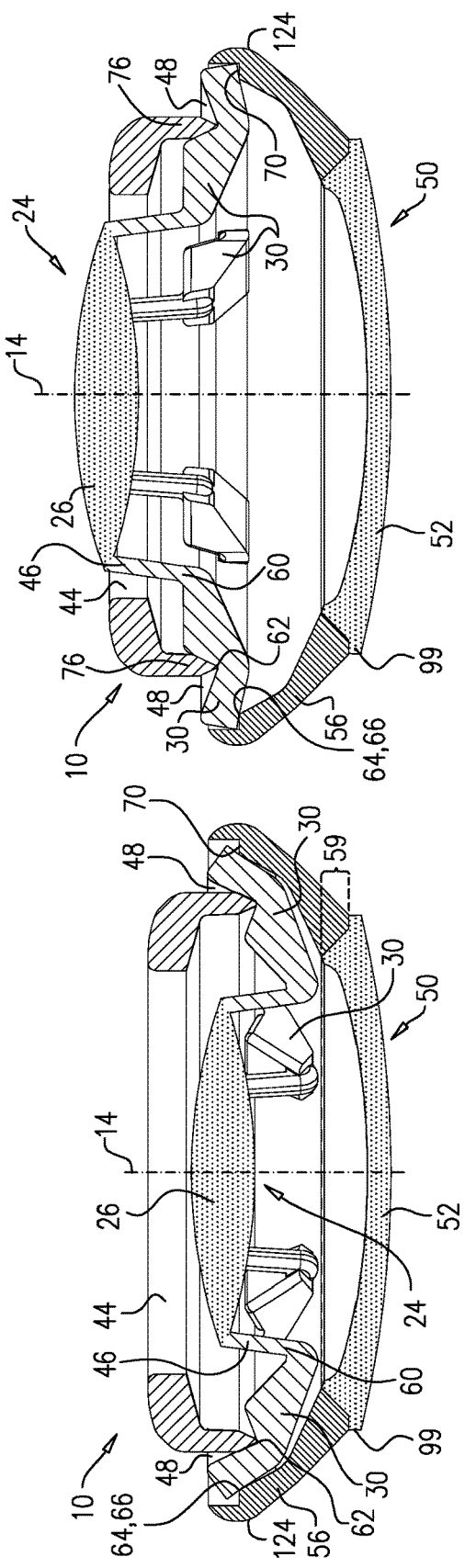

ACCOMMODATIVE INTRAOCULAR LENS

FIELD OF THE APPLICATION

The present invention relates generally to implantable medical devices, and specifically to intraocular lenses.

BACKGROUND OF THE APPLICATION

Accommodating intraocular lenses (AIOLs) allow the eye to focus at different distances. The Crystalens® (Bausch & Lomb, Rochester, N.Y., USA) is an AIOL that has received FDA approval in the United States.

US Patent Application Publication 2011/0071628 to Gross et al. describes an accommodating intraocular lens (AIOL) implant that includes at least an anterior floating lens complex and a posterior lens complex, each of which comprises one or more optical elements, and a frame comprising one or more levers, which are coupled to the frame and the anterior floating lens complex. The levers are configured to leverage motion of the frame to move the anterior floating lens complex with respect to the posterior lens complex. Other embodiments are also described.

US Patent Application Publication 2014/0309735 to Sohn et al., which is incorporated herein by reference, describes an accommodating intraocular lens implant that includes an anterior floating lens unit, a posterior lens unit, an anterior lens link, and an anterior rim link, which comprises an anterior rim jointed element. An anterior rim complex is disposed such that the anterior floating lens unit is movable toward and away from the anterior rim complex, in an anterior-posterior direction. A lever is connected (a) at a first longitudinal site along the lever, to the anterior floating lens unit by the anterior lens link, and (b) at a second longitudinal site along the lever, to the anterior rim complex by the anterior rim link. The lever, at a third longitudinal site along the lever, is in jointed connection with the posterior lens unit. The second site is longitudinally between the first and the third sites along the lever.

PCT Publication WO 2015/198236 to Sohn et al., which is incorporated herein by reference, describes an accommodating intraocular lens implant that includes an anterior floating lens unit, a posterior lens unit, an anterior rim complex disposed such that the anterior floating lens unit is movable toward and away from the anterior rim complex. A plurality of levers are in jointed connection with: the anterior floating lens unit at respective first longitudinal sites along the levers, the anterior rim complex at respective second longitudinal sites along the levers, and the posterior lens unit at respective third longitudinal sites along the levers. For each of the levers, (a) a line defined by the second and third longitudinal sites, if projected onto a plane defined by a radially-outer perimeter of the lens implant, and (b) a line tangential to the radially-outer perimeter of the lens implant at a circumferential site of the perimeter circumferentially corresponding to the third longitudinal site, form an angle of between 75 and 105 degrees.

SUMMARY OF THE APPLICATION

In some applications of the present invention, an accommodative intraocular lens implant is shaped so as to be assemblable into an assembled state in situ in a capsular bag of a human eye so as to have a central optical axis. The lens implant comprises an anterior floating lens unit, which comprises an anterior lens; a posterior lens unit, which comprises a posterior lens; an anterior rim; and levers. When the lens implant is in the assembled state, the levers are, (a) (i) in pivotable contact with the anterior floating lens unit at respective first longitudinal sites along the levers, (ii) in pivotable contact with the anterior rim at respective second longitudinal sites along the levers, and (iii) in pivotable contact with the posterior lens unit at respective third longitudinal sites along the levers, and (b) arranged to move the anterior floating lens unit toward and away from the anterior rim, in an anterior-posterior direction, wherein, for each respective lever of the levers, the second longitudinal site is farther from the central optical axis than the first longitudinal site is from the central optical axis, and the third longitudinal site is farther from the central optical axis than the second longitudinal site is from the central optical axis.

The lens implant further comprises a circumferential rim, which is attached to the levers such that at least a portion of the circumferential rim is farther from the central optical axis than the second longitudinal sites are from the central optical axis. The lens implant is arranged such that in the assemble state elastic potential energy is stored in the lens implant as a result of deformation of the lens implant during a transition from a fully-accommodated state to a fully-unaccommodated state, and at least 50% of the elastic potential energy stored in the lens implant as the result of the deformation is stored in the circumferential rim.

The lens implant's accommodation typically provides a continuous range of focus, including near, distance; and intermediate distances. The lens implant exploits the natural accommodation mechanism of the eye, which reacts in order to sharpen the image on the retina. The lens implant thus typically reduces the need for glasses, which are generally required by patients with conventional IOLs. The lens implant is typically implanted in the eye after natural lens removal because of cataract, or for Refractive Lens Exchange (RLE), using well-known IOL implantation techniques, including making a small incision.

There is therefore provided, in accordance with an application of the present invention, apparatus including an accommodating intraocular lens implant, which is shaped so as to be assemblable into an assembled state in situ in a capsular bag of a human eye so as to have a central optical axis, and which includes:

an anterior floating lens unit, which includes an anterior lens;

a posterior lens unit, which includes a posterior lens;

an anterior rim;

levers, which are, when the lens implant is in the assembled state, (a) (i) in pivotable contact with the anterior floating lens unit at respective first longitudinal sites along the levers, (ii) in pivotable contact with the anterior rim at respective second longitudinal sites along the levers, and (iii) in pivotable contact with the posterior lens unit at respective third longitudinal sites along the levers, and (b) arranged to move the anterior floating lens unit toward and away from the anterior rim, in an anterior-posterior direction, wherein, for each respective lever of the levers, the second longitudinal site is farther from the central optical axis than the first longitudinal site is from the central optical axis, and the third longitudinal site is farther from the central optical axis than the second longitudinal site is from the central optical axis; and a circumferential rim, which is attached to the levers such that at least a portion of the circumferential rim is farther from the central optical axis than the second longitudinal sites are from the central optical axis, wherein the lens implant is arranged such that in the assemble state:

elastic potential energy is stored in the lens implant as a result of deformation of the lens implant during a transition from a fully-accommodated state to a fully-unaccommodated state, and at least 50% of the elastic potential energy stored in the lens implant as the result of the deformation is stored in the circumferential rim.

For some applications, the lens implant is arranged when in the assembled state such that at least 70% of the elastic potential energy stored in the lens implant as the result of the deformation is stored in the circumferential rim.

For some applications, the lens implant is arranged when in the assembled state such that at least 90% of the elastic potential energy stored in the lens implant as the result of the deformation is stored in the circumferential rim.

For some applications, the lens implant is arranged when in the assembled state such that less than 10% of the elastic potential energy in aggregate is stored in the levers at the second longitudinal sites, at respective interfaces between the levers and the anterior rim, and in the anterior rim, in aggregate.

For some applications, the lens implant is arranged when in the assembled state such that none of the elastic potential energy in aggregate is stored in the levers at the second longitudinal sites, at the respective interfaces between the levers and the anterior rim, and in the anterior rim, in aggregate.

For some applications, the lens implant is arranged when in the assembled state such that less than 10% of the elastic potential energy in aggregate is stored at respective interfaces between the levers and the posterior lens unit, and in the posterior lens unit, in aggregate.

For some applications, the lens implant is arranged when in the assembled state such that none of the elastic potential energy in aggregate is stored at the respective interfaces between the levers and the posterior lens unit, and in the posterior lens unit, in aggregate.

For some applications, the levers, when the lens implant is in the assembled state, are in non-jointed pivotable contact with the anterior rim at the respective second longitudinal sites along the levers.

For some applications, the levers, when the lens implant is in the assembled state, are in non-jointed pivotable contact with the posterior lens unit at the respective third longitudinal sites along the levers.

For some applications, the levers, when the lens implant is in the assembled state, are in jointed pivotable connection with the anterior floating lens unit at the respective first longitudinal sites along the levers.

For some applications:

the lens implant further includes anterior lens jointed elements, and the levers are in the jointed pivotable connection, at the respective first longitudinal sites along the levers, with the anterior floating lens unit by the anterior lens jointed elements, respectively.

For some applications, the lens implant is arranged when in the assembled state such that less of the elastic potential energy in aggregate is stored (a) in the levers at the second longitudinal sites, at respective interfaces between the levers and the anterior rim, and in the anterior rim, in aggregate than (b) in the levers at the first longitudinal sites, at respective interfaces between the levers and the anterior floating lens unit, and in the anterior lens jointed elements, in aggregate.

For some applications, the levers and the anterior rim are not shaped to provide a snapping interface therebetween.

For some applications, the lens implant is arranged when in the assembled state such that at least 50% of the elastic potential energy stored in the lens implant as the result of the deformation is stored in a volume of the circumferential rim, the volume equal to at least 4 mm3.

For some applications, the lens implant is arranged when in the assembled state such that at least 50% of the elastic potential energy stored in the lens implant as the result of the deformation is stored in a volume of the circumferential rim, the volume equal to at least 5% of a total volume of all solid elements of the lens implant, excluding empty spaces defined by the lens implant.

For some applications, a radially-outer perimeter of the lens implant is defined by the posterior lens unit.

For some applications, the levers are shaped so as to define respective indentations on respective anterior sides at the respective second longitudinal sites, and the anterior rim pivotably contacts the respective indentations when the lens implant is in the assembled state.

For some applications, the circumferential rim is arranged in pivotable contact with the posterior lens unit when the lens implant is in the assembled state.

For some applications, the circumferential rim is arranged in non-jointed pivotable contact with the posterior lens unit when the lens implant is in the assembled state.

For some applications, the circumferential rim is arranged in the pivotable contact with the posterior lens unit around an entire circumference of the circumferential rim when the lens implant is in the assembled state.

For some applications, the circumferential rim and the posterior lens unit are not shaped to provide a snapping interface therebetween.

For some applications, the lens implant is arranged when in the assembled state such that less than 10% of the elastic potential energy in aggregate is stored at one or more interfaces between the circumferential rim and the posterior lens unit, and in the posterior lens unit, in aggregate.

For some applications, the lens implant is arranged when in the assembled state such that none of the elastic potential energy in aggregate is stored at the one or more interfaces between the circumferential rim and the posterior lens unit, and in the posterior lens unit, in aggregate.

For some applications, the circumferential rim is attached to the levers such that the entire circumferential rim is farther from the central optical axis than the second longitudinal sites are from the central optical axis.

For some applications, the lens implant is arranged when in the assembled state such that the elastic potential energy stored in the circumferential rim is stored around at least 270 degrees of the circumferential rim.

For some applications, the lens implant is arranged when in the assembled state such that the elastic potential energy stored in the circumferential rim is stored around 360 degrees of the circumferential rim.

For some applications, when the lens implant is in the assembled state:

the posterior lens unit is shaped so as to define one or more ledges that face anteriorly, and the levers are in the pivotable contact with the one or more ledges at the respective third longitudinal sites along the levers.

For some applications, the circumferential rim is in pivotable contact with the one or more ledges.

For some applications, the posterior lens unit is shaped so as to define a single ledge that extends around an entire circumference of the posterior lens unit.

For some applications, the one or more ledges define one or more respective radially-inward edges, and the levers are in pivotable contact with the one or more radially-inward edges at the respective third longitudinal sites along the levers when the lens implant is in the assembled state.

For some applications, the posterior lens unit is shaped so as to define a circumferential lip that extends anteriorly beyond the one or more ledges, and the one or more ledges project from the circumferential lip radially inward toward the central optical axis.

For some applications, the lens implant is arranged such that in the assembled state:

a surface defined by the circumferential rim faces at least partially anteriorly when the lens implant is in the fully-accommodated state, and the surface rotates toward the central optical axis during the transition from the fully-accommodated state to the fully-unaccommodated state.

For some applications, the lens implant is arranged such that in the assembled state:

during the transition from the fully-accommodated state to the fully-unaccommodated state, the circumferential rim rotates about a circumferential axis thereof in a first rotational direction, thereby storing elastic potential energy, and during a transition from the fully-unaccommodated state to the fully-accommodated state, the circumferential rim rotates about the circumferential axis in a second rotational direction opposite the first rotational direction, thereby releasing the stored elastic potential energy.

There is further provided, in accordance with an application of the present invention, apparatus including an accommodating intraocular lens implant, which is shaped so as to be assemblable into an assembled state in situ in a capsular bag of a human eye so as to have a central optical axis, and which includes:

an anterior floating lens unit, which includes an anterior lens;

a posterior lens unit, which includes a posterior lens;

an anterior rim; and levers, which are, when the lens implant is in the assembled state, (a) (i) in pivotable contact with the anterior floating lens unit at respective first longitudinal sites along the levers, (ii) in non-jointed pivotable contact with the anterior rim at respective second longitudinal sites along the levers, and (iii) in pivotable contact with the posterior lens unit at respective third longitudinal sites along the levers, and (b) arranged to move the anterior floating lens unit toward and away from the anterior rim, in an anterior-posterior direction, wherein, for each respective lever of the levers, the second longitudinal site is farther from the central optical axis than the first longitudinal site is from the central optical axis, and the third longitudinal site is farther from the central optical axis than the second longitudinal site is from the central optical axis.

For some applications, the levers, when the lens implant is in the assembled state, are in non-jointed pivotable contact with the posterior lens unit at the respective third longitudinal sites along the levers.

For some applications, the levers and the anterior rim are not shaped to provide a snapping interface therebetween.

For some applications, the levers, when the lens implant is in the assembled state, are in jointed pivotable connection with the anterior floating lens unit at the respective first longitudinal sites along the levers.

For some applications:

the lens implant further includes anterior lens jointed elements, and the levers are in the jointed pivotable connection, at the respective first longitudinal sites along the levers, with the anterior floating lens unit by the anterior lens jointed elements, respectively.

For some applications, the lens implant further includes a circumferential rim, which is attached to the levers such that at least a portion of the circumferential rim is farther from the central optical axis than the second longitudinal sites are from the central optical axis.

For some applications, the lens implant is arranged such that in the assembled state:

elastic potential energy is stored in the lens implant as a result of deformation of the lens implant during a transition from a fully-accommodated state to a fully-unaccommodated state, and at least 50% of the elastic potential energy stored in the lens implant as the result of the deformation is stored in the circumferential rim.

For some applications, the circumferential rim is arranged in pivotable contact with the posterior lens unit when the lens implant is in the assembled state.

For some applications, the circumferential rim is arranged in non-jointed pivotable contact with the posterior lens unit when the lens implant is in the assembled state.

For some applications, the circumferential rim is arranged in the pivotable contact with the posterior lens unit around an entire circumference of the circumferential rim when the lens implant is in the assembled state.

For some applications, the circumferential rim and the posterior lens unit are not shaped to provide a snapping interface therebetween.

For some applications, the circumferential rim is attached to the levers such that the entire circumferential rim is farther from the central optical axis than the second longitudinal sites are from the central optical axis.

For some applications, when the lens implant is in the assembled state:

the posterior lens unit is shaped so as to define one or more ledges that face anteriorly, and the levers are in the pivotable contact with the one or more ledges at the respective third longitudinal sites along the levers.

For some applications, the posterior lens unit is shaped so as to define a single ledge that extends around an entire circumference of the posterior lens unit.

For some applications, the one or more ledges define one or more respective radially-inward edges, and the levers are in pivotable contact with the one or more radially-inward edges at the respective third longitudinal sites along the levers when the lens implant is in the assembled state.

For some applications, the posterior lens unit is shaped so as to define a circumferential lip that extends anteriorly beyond the one or more ledges, and the one or more ledges project from the circumferential lip radially inward toward the central optical axis.

There is still further provided, in accordance with an application of the present invention, apparatus including an accommodating intraocular lens implant, which is shaped so as to be assemblable into an assembled state in situ in a capsular bag of a human eye so as to have a central optical axis, and which includes:

a first posterior component, which includes a posterior lens unit, which includes a posterior lens;

a second posterior component, which includes a posterior lens rim;

a first anterior component, which includes:

an anterior floating lens unit, which includes an anterior lens; and levers; and a second anterior component, which includes an anterior rim, wherein the levers are, when the lens implant is in the assembled state, (a) (i) in pivotable contact with the anterior floating lens unit at respective first longitudinal sites along the levers, (ii) in pivotable contact with the anterior rim at respective second longitudinal sites along the levers, and (iii) in pivotable contact with the posterior lens unit at respective third longitudinal sites along the levers, and (b) arranged to move the anterior floating lens unit toward and away from the anterior rim, in an anterior-posterior direction, and wherein the first posterior component, the second posterior component, the first anterior component, and the second anterior component are not integral with one another, and are shaped so as to be assemblable into the assembled state iii 11 with one another in a capsular bag of a human eye.

For some applications, wherein, for each respective lever of the levers, the second longitudinal site is farther from a central optical axis of the lens implant than the first longitudinal site is from the central optical axis, and the third longitudinal site is farther from the central optical axis than the second longitudinal site is from the central optical axis.

For some applications, the levers, when the lens implant is in the assembled state, are in jointed pivotable connection with the anterior floating lens unit at the respective first longitudinal sites along the levers.

For some applications, the levers, when the lens implant is in the assembled state, are in non-jointed pivotable contact with the anterior rim at the respective second longitudinal sites along the levers.

For some applications, the levers and the anterior rim are not shaped to provide a snapping interface therebetween.

For some applications, the levers are shaped so as to define respective indentations on respective anterior sides at the respective second longitudinal sites, and the anterior rim pivotably contacts the respective indentations when the lens implant is in the assembled state.

For some applications, the levers, when the lens implant is in the assembled state, are in non-jointed pivotable contact with the posterior lens unit at the respective third longitudinal sites along the levers.

For some applications, the lens implant further includes a circumferential rim, which is attached to the levers such that at least a portion of the circumferential rim is farther from a central optical axis of the lens implant than the second longitudinal sites are from the central optical axis.

For some applications, the lens implant is arranged such that in the assembled state:

elastic potential energy is stored in the lens implant as a result of deformation of the lens implant during a transition from a fully-accommodated state to a fully-unaccommodated state, and at least 50% of the elastic potential energy stored in the lens implant as the result of the deformation is stored in the circumferential rim.

For some applications, the circumferential rim is attached to the levers such that the entire circumferential rim is farther from the central optical axis than the second longitudinal sites are from the central optical axis.

For some applications, the circumferential rim is arranged in pivotable contact with the posterior lens unit when the lens implant is in the assembled state.

For some applications, the circumferential rim is arranged in non-jointed pivotable contact with the posterior lens unit when the lens implant is in the assembled state.

For some applications, the circumferential rim is arranged in the pivotable contact with the posterior lens unit around an entire circumference of the circumferential rim when the lens implant is in the assembled state.

For some applications, the circumferential rim and the posterior lens unit are not shaped to provide a snapping interface therebetween.

For some applications, when the lens implant is in the assembled state:

the posterior lens unit is shaped so as to define one or more ledges that face anteriorly, and the levers are in the pivotable contact with the one or more ledges at the respective third longitudinal sites along the levers.

For some applications, the posterior lens unit is shaped so as to define a single ledge that extends around an entire circumference of the posterior lens unit.

For some applications, the one or more ledges define one or more respective radially-inward edges, and the levers are in pivotable contact with the one or more radially-inward edges at the respective third longitudinal sites along the levers when the lens implant is in the assembled state.

For some applications, the posterior lens unit is shaped so as to define a circumferential lip that extends anteriorly beyond the one or more ledges, and the one or more ledges project from the circumferential lip radially inward toward the central optical axis.

For some applications, the apparatus further includes an introducer system, which includes:

a first posterior introducer tube, in which the first posterior component is removably disposed;

a second posterior introducer tube, in which the second posterior component is removably disposed;

a first anterior introducer tube, in which the first anterior component is removably disposed; and a second anterior introducer tube, in which the second anterior component is removably disposed, and the first posterior introducer tube, the second posterior introducer tube, the first anterior introducer tube, and the second anterior introducer tube are distinct and separate from each other.

For some applications, each of the first posterior introducer tube, the second posterior introducer tube, the first anterior introducer tube, and the second anterior introducer tube has an outer diameter of no more than 3 mm.

For some applications, the apparatus further includes an introducer system, which includes one or more introducer tubes, in which the first posterior component, the second posterior component, the first anterior component, and the second anterior component are removably disposed at respective axial positions that do not axially overlap with one another.

For some applications, each of the one or more introducer tubes has an outer diameter of no more than 3 mm.

There is additionally provided, in accordance with an application of the present invention, a method including:

providing an accommodating intraocular lens implant, which is shaped so as to be assemblable into an assembled state in situ in a capsular bag of a human eye so as to have a central optical axis, and which includes (a) a first posterior component, which includes a posterior lens unit, which includes a posterior lens; (b) a second posterior component, which includes a posterior lens rim; (c) a first anterior component, which includes (i) an anterior floating lens unit, which includes an anterior lens; and (ii) levers; and (d) a second anterior component, which includes an anterior rim,
  wherein the levers are, when the lens implant is in the assembled state, (A) (1) in pivotable contact with the anterior floating lens unit at respective first longitudinal sites along the levers, (2) in pivotable contact with the anterior rim at respective second longitudinal sites along the levers; and (3) in pivotable contact with the posterior lens unit at respective third longitudinal sites along the levers, and (B) arranged to move the anterior floating lens unit toward and away from the anterior rim, in an anterior-posterior direction, and
  wherein the first posterior component, the second posterior component, the first anterior component, and the second anterior component are not integral with one another; and
 separately inserting each of the first posterior component, the second posterior component, the first anterior component, and the second anterior component into the capsular bag of the human eye and assembling the first posterior component, the second posterior component, the first anterior component, and the second anterior component into the assembled state in situ with one another in the capsular bag.

For some applications, separately inserting including:
  inserting the first posterior component before or after inserting the second posterior component;
  thereafter, inserting the first anterior component; and
  thereafter, inserting the second anterior component.

For some applications:
  the lens implant further includes a circumferential rim, which is attached to the levers such that at least a portion of the circumferential rim is farther from a central optical axis of the lens implant than the second longitudinal sites are from the central optical axis, and
  assembling the first posterior component, the second posterior component, the first anterior component, and the second anterior component does not include snapping the circumferential rim into the posterior lens unit.

For some applications:
  the method further includes providing an introducer system, which includes (a) a first posterior introducer tube, in which the first posterior component is removably disposed; (b) a second posterior introducer tube, in which the second posterior component is removably disposed; (c) a first anterior introducer tube, in which the first anterior component is removably disposed; and (d) a second anterior introducer tube, in which the second anterior component is removably disposed, wherein the first posterior introducer tube, the second posterior introducer tube, the first anterior introducer tube, and the second anterior introducer tube are distinct and separate from each other, and
  separately inserting each of the first posterior component, the second posterior component, the first anterior component, and the second anterior component into the capsular bag includes:
    inserting the first posterior introducer tube into the capsular bag, and releasing the first posterior component from the first posterior introducer tube in the capsular bag;
    inserting the second posterior introducer tube into the capsular bag, and releasing the second posterior component from the second posterior introducer tube in the capsular bag;
    thereafter, assembling together the posterior lens and the posterior lens rim in situ in the capsular bag such that the posterior lens rim radially surrounds at least an axial portion of the posterior lens;
    thereafter, inserting the first anterior introducer tube into the capsular bag, releasing the first anterior component from first anterior introducer tube in the capsular bag, and placing the anterior floating lens unit in contact with the posterior lens rim; and
    thereafter, inserting the second anterior introducer tube into the capsular bag, releasing the second anterior component from the second anterior introducer tube, and placing the anterior rim in pivotable contact with the levers.

For some applications, each of the first posterior introducer tube, the second posterior introducer tube, the first anterior introducer tube, and the second anterior introducer tube has an outer diameter of no more than 3 mm.

For some applications:
  the method further includes providing an introducer system, which includes one or more introducer tubes, in which the first posterior component, the second posterior component, the first anterior component, and the second anterior component are removably disposed at respective axial positions that do not axially overlap with one another, and
  separately inserting each of the first posterior component, the second posterior component, the first anterior component, and the second anterior component into the capsular bag includes using the one or more introducer tubes to separately insert each of the first posterior component, the second posterior component, the first anterior component, and the second anterior component into the capsular bag.

The present invention will be more fully understood from the following detailed description of embodiments thereof, taken together with the drawings, in which:

BRIEF DESCRIPTION OF THE DRAWINGS

FIGS. 3A-B are schematic illustration of components of the lens implant of FIGS. 1A-C and 2A-C prior to assembly and after assembly into an assembled state, respectively, in accordance with an application of the present invention;

FIGS. 4A-B are schematic cross-sectional illustrations of the lens implant of FIGS. 1A-C and 2A-C in a fully-unaccommodated state and a fully-accommodated state, respectively, in accordance with an application of the present invention;

DETAILED DESCRIPTION OF APPLICATIONS

Figure 1A:
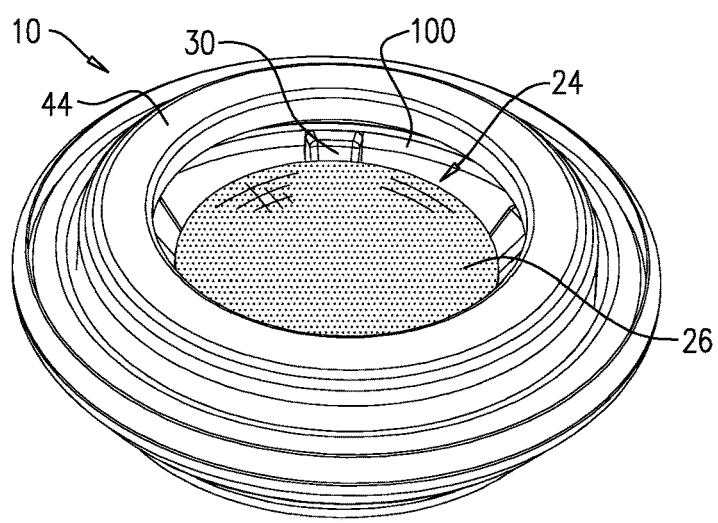
FIGS. 1A-C are schematic illustrations of an accommodative intraocular lens implant, in accordance with an application of the present invention.
Figure 1B:
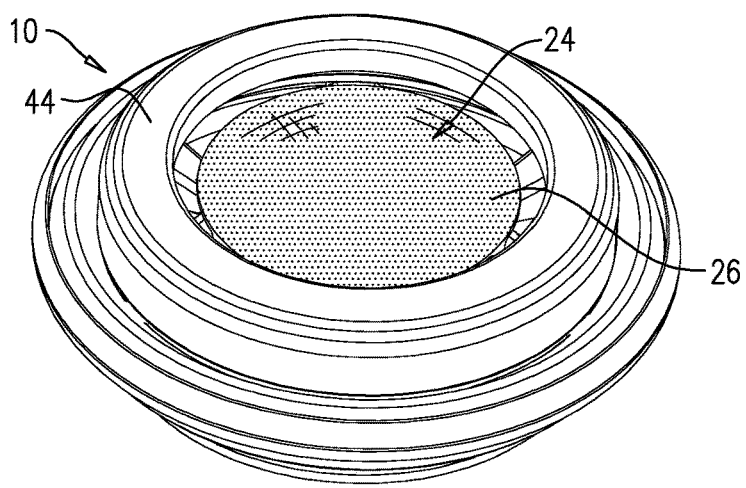
Figure 1C:
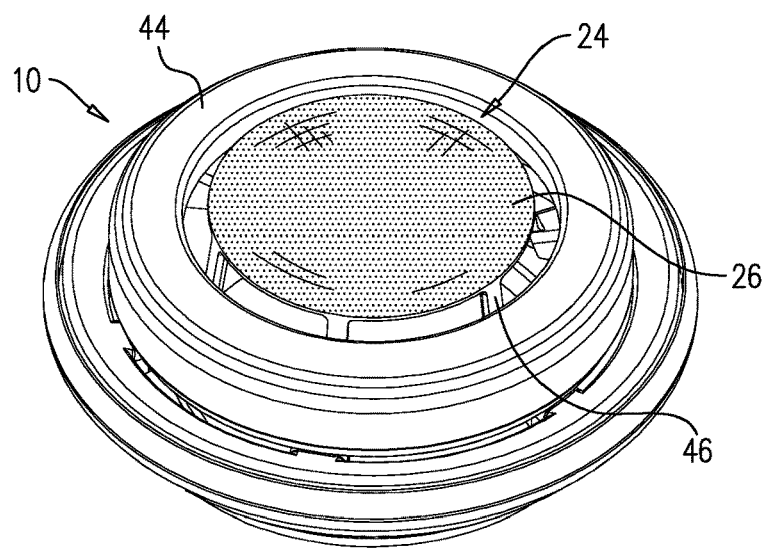
Figure 2A:
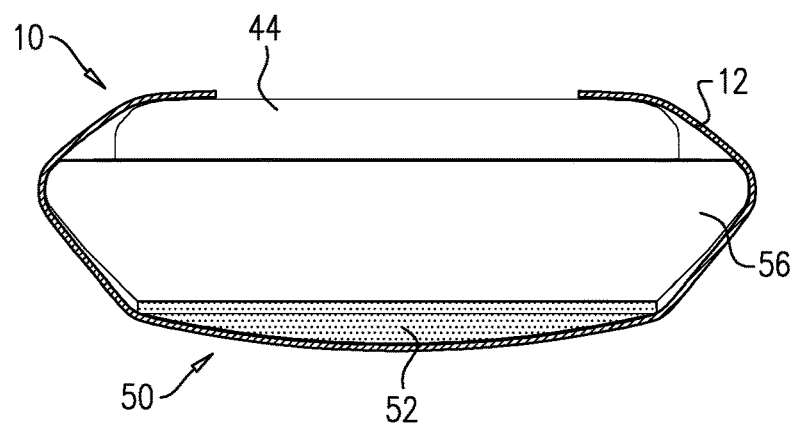
FIGS. 2A-C are schematic illustrations of the lens implant of FIGS. 1A-C implanted in a natural capsular bag of the eye, in accordance with an application of the present invention.
Figure 2B:
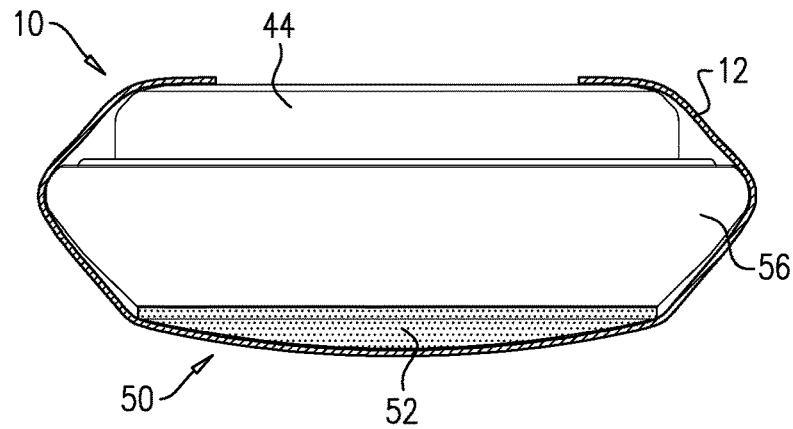
Figure 2C:
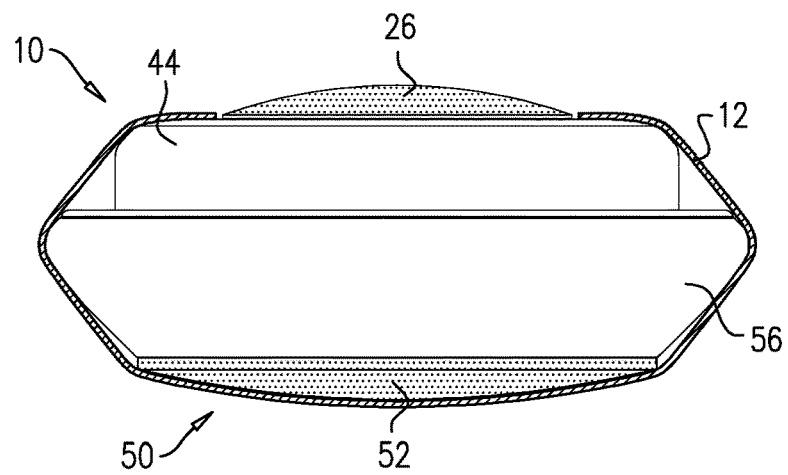

FIGS. 1A-C and 2A-C are schematic illustrations of an accommodative intraocular lens implant 10, in accordance with an application of the present invention. FIGS. 1A-C are isometric views of the lens implant. FIGS. 2A-C are side views showing the lens implant implanted in a natural capsular bag 12 of a human eye. FIGS. 1A and 2A show lens implant 10 in a fully-unaccommodated state, FIGS. 1B and 2B show lens implant 10 in a partially-accommodated state, and FIGS. 1C and 2C show the lens implant in a fully-accommodated state. Although only these three states are shown in these and some of the other figures, lens implant 10 is configured to assume a continuous range of accommodation between the fully-unaccommodated state and the fully-accommodated state. The fully-accommodated state provides near vision, the fully-unaccommodated state provides distance vision, and partially-accommodated states therebetween provide intermediate vision. The lens implant is configured to reach the fully-accommodated state responsively to the natural accommodation mechanism of the eye, without the need for external power.

Reference is still made to FIGS. 1A-C and 2A-C, and is additionally made to FIGS. 3A-B, which are schematic illustration of components of lens implant 10 prior to assembly and after assembly into an assembled state, respectively, in accordance with an application of the present invention. Typically, lens implant 10 is shaped so as to be assemblable into the assembled state in situ in capsular bag 12 so as to have a central optical axis 14.

Reference is still made to FIGS. 1A-C, 2A-C, and 3A-B, and is additionally made to FIGS. 4A-B, which are schematic cross-sectional illustrations of lens implant 10 in the fully-unaccommodated state and the fully-accommodated state, respectively, in accordance with an application of the present invention. Lens implant 10 comprises (a) an anterior floating lens unit 24, which comprises an anterior lens 26; (b) levers 30; (c) an anterior rim 44; (d) a circumferential rim 48; and (e) a posterior lens unit 50, which comprises a posterior lens 52.

For some applications, when lens implant 10 is in the assembled state, such as shown in FIGS. 1A-C, 2A-C, 3B, and 4A-B, levers 30 are:
  in pivotable contact with anterior floating lens unit 24 at respective first longitudinal sites 60 along levers 30,
  in pivotable contact with anterior rim 44 at respective second longitudinal sites 62 along levers 30, and
  in pivotable contact with posterior lens unit 50 at respective third longitudinal sites 64 along levers 30.
(The phrase "along" lever 30 is to be understood as including the ends of the lever.)

Levers 30 are arranged to move anterior floating lens unit 24 toward and away from anterior rim 44, in an anterior-posterior direction. For some applications, lens implant 10 comprises between three and eight levers 30, such as three, four, five, or six levers 30. For some applications, posterior lens unit 50 is bowl-shaped and/or concave and has an inner surface, which may be shaped such that the inner surface limits posterior motion of anterior floating lens unit 24.

For some applications, such as shown in the figures, for each respective lever 30 of levers 30, second longitudinal site 62 is farther from central optical axis 14 than first longitudinal site 60 is from central optical axis 14, and third longitudinal site 64 is farther from central optical axis 14 than second longitudinal site 62 is from central optical axis 14. As is universally known in the art, the distance between a point and an axis is measured along a line perpendicular to the axis extending from the point to the axis. As applied in the present application, including in the claims, all distances to central optical axis 14 are measured perpendicular to central optical axis 14.

Typically, circumferential rim 48 is attached to levers 30 such that at least a portion of (such as the entire, as shown in the figures) circumferential rim 48 is farther from central optical axis 14 than second longitudinal sites 62 are from central optical axis 14.

Figure 5B:
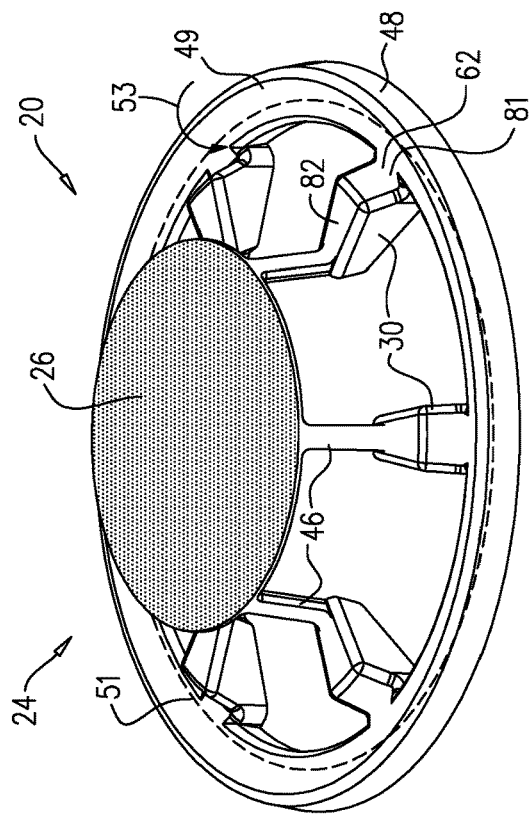
FIGS. 5A-B are schematic cross-sectional illustrations of a circumferential rim of the lens implant of FIGS. 1A-C when the lens implant is in the fully-unaccommodated state and the fully-accommodated state, respectively, in accordance with an application of the present invention.
Figure 5A:
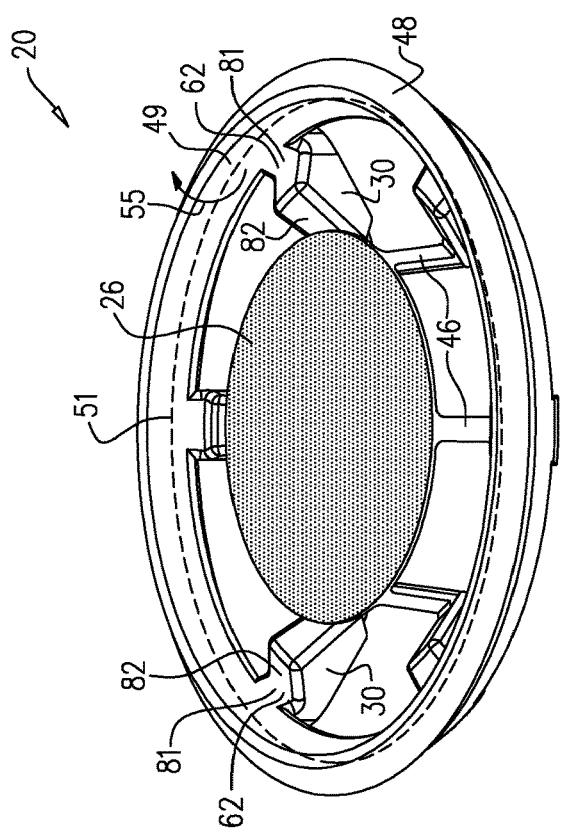

Reference is still made to FIGS. 1A-C, 2A-C, 3A-B, and 4A-C, and is additionally made to FIGS. 5A-B, which are schematic cross-sectional illustrations of circumferential rim 48 when lens implant 10 is in the fully-unaccommodated state and the fully-accommodated state, respectively, in accordance with an application of the present invention. For some applications, lens implant 10 is arranged such that in the assemble state:
  elastic potential energy is stored in lens implant 10 as a result of deformation of lens implant 10 during a transition from the fully-accommodated state, such as shown in FIGS. 1C, 2C, and 4B, to the fully-unaccommodated state, such as shown in FIGS. 1A, 2A, and 3A (elastic potential energy is of course also stored during any decrease in accommodation of the lens implant), and
  at least 50% (e.g., at least 70%, such as at least 90%) of the elastic potential energy stored in lens implant 10 as the result of the deformation is stored in circumferential rim 48.

In other words, circumferential rim 48 functions as a spring that provides at least 50% (e.g., at least 70%, such as at least 90%) of the energy storage of lens implant 10 during the transition from the fully-accommodated state to the fully-unaccommodated state. For some applications, lens implant 10 is arranged when in the assembled state such that the elastic potential energy stored in circumferential rim 48 is stored around at least 270 degrees, typically 360 degrees, of circumferential rim 48. This arrangement allows circumferential rim 48 to store a large amount of energy relative to the size of lens implant 10, which generally minimizes the impact of any manufacturing inconsistencies.

As a result of this springiness, the resting state of the lens implant is typically the fully-accommodated state, or, optionally, slightly beyond the fully-accommodated state, such that the lens implant is always pressing the lens capsule open even when the lens implant is fully accommodated, thereby keeping the zonules in tension.

By contrast, PCT Publication WO 2015/198236, which is incorporated herein by reference, describes an accommodative intraocular lens implant 210 with reference to FIGS. 16A-24 thereof. The inventors estimate that in accommodative intraocular lens implant 210, only about 20% of the elastic potential energy stored in the lens implant as the result of deformation of the lens implant is stored in the circumferential rim 260. In fact, circumferential rim 260 is illustrated as being shaped so as to define pairs of notches 276 on both circumferential sides of each of levers 250 at the site at which the lever is attached to the circumferential rim. These notches are described as allowing the levers to rotate about respective joints with the posterior lens unit 222, thereby obviating any need for the entire circumferential rim to rotate. The inventors also estimate that in accommodative intraocular lens implant 210, at least 70% of the elastic potential energy stored in the lens implant as the result of deformation of the lens implant is stored in the jointed connection between levers 30 and anterior rim complex 225 at the respective second longitudinal sites 254 along levers 250, by the respective anterior rim links 230.

For some applications, lens implant 10 is arranged when in the assembled state such that at least 50% (e.g., at least 70%, such as at least 90%) of the elastic potential energy stored in lens implant 10 as the result of the deformation is stored in a volume of circumferential rim 48, the volume equal to at least 4 mm3, e.g., at least 7 mm3. Alternatively or additionally, for some applications, lens implant 10 is arranged when in the assembled state such that at least 50% (e.g., at least 70%, such as at least 90%) of the elastic potential energy stored in lens implant 10 as the result of the deformation is stored in a volume of circumferential rim 48, the volume equal to at least 5% (e.g., at least 10%) of a total volume of all solid elements of lens implant 10, excluding empty spaces defined by lens implant 10.

For some applications, lens implant 10 is arranged such that in the assembled state (a) a surface 49 (labeled in FIGS. 5A-B) defined by circumferential rim 48 faces at least partially anteriorly when lens implant 10 is in the fully-accommodated state, such as shown in FIGS. 1C, 2C, and 4B, and (b) surface 49 rotates toward central optical axis 14 during the transition from the fully-accommodated state to the fully-unaccommodated state, such as shown in FIGS. 1A, 2A, and 3A. Typically, lens implant 10 is arranged such that in the assembled state (a) during the transition from the fully-accommodated state to the fully-unaccommodated state, circumferential rim 48 rotates about a circumferential axis 51 thereof in a first rotational direction (indicated in FIG. 5B by a first arrow 53), thereby storing elastic potential energy, and (b) during a transition from the fully-unaccommodated state to the fully-accommodated state, circumferential rim rotates about circumferential axis 51 in a second rotational direction (indicated in FIG. 5A by a second arrow 55) opposite the first rotational direction, thereby releasing the stored elastic potential energy.

Lens implant 10 is typically arranged when in the assembled state such that less than 10% (e.g., less than 5%, such as none) of the elastic potential energy in aggregate is stored in levers 30 at second longitudinal sites 62, at respective interfaces between levers 30 and anterior rim 44, and in anterior rim 44, in aggregate (i.e., the sum of the elastic potential energy stored in levers 30 at second longitudinal sites 62, at respective interfaces between levers 30 and anterior rim 44, and in anterior rim 44). This relatively low storage of elastic potential energy may be because, in some configurations, levers 30, when lens implant 10 is in the assembled state, are in non-jointed pivotable contact with anterior rim 44 at the respective second longitudinal sites 62 along levers 30, and anterior rim 44 does not materially bend or deform during accommodation of lens implant 10, but instead acts as a generally rigid body. As used in the present application, including in the claims, two elements are in "non-jointed pivotable contact" if the two elements can pivot with respect to each other but are not integrally attached to each other or interlocked with each other; the two elements would thus come apart if not held together by other elements of lens implant 10, by capsular bag 12, by gravity, or by anything else. As used in the present application, including in the claims, two elements are "integrally attached" to each other if they are physically merged together (such as by melting), attached by an adhesive, or fabricated from and remain a single piece; likewise, two elements are "not integral" with one another if they are not integrally attached (for example, if they are simply placed in contact with each other).

Similarly, lens implant 10 is typically arranged when in the assembled state such that less than 10% (e.g., less than 5%, such as none) of the elastic potential energy in aggregate is stored at respective interfaces between levers 30 and posterior lens unit 50, and in posterior lens unit 50, in aggregate the sum of the elastic potential energy stored at respective interfaces between levers 30 and posterior lens unit 50, and in posterior lens unit 50). This relatively low storage of elastic potential energy may be because, in some configurations, levers 30, when lens implant 10 is in the assembled state, are in non jointed pivotable contact with posterior lens unit 50 at the respective third longitudinal sites 64 along levers 30, and posterior lens unit 50 does not materially bend or deform during accommodation of lens implant 10, but instead acts as a generally rigid body.

Typically, lens implant 10 is arranged when in the assembled state such that less of the elastic potential energy in aggregate is stored (a) in levers 30 at second longitudinal sites 62, at respective interfaces between levers 30 and anterior rim 44, and in anterior rim 44, in aggregate than (b) in levers 30 at first longitudinal sites 60, at respective interfaces between levers 30 and anterior floating lens unit 24, and in anterior lens jointed elements 46, in aggregate.

For some applications, levers 30, when lens implant 10 is in the assembled state, are in jointed pivotable connection with anterior floating lens unit 24 at the respective first longitudinal sites 60 along levers 30. As used in the present application, including in the claims, two elements are in "jointed pivotable connection" if the two elements can pivot with respect to each other and are integrally attached to each other or interlocked with each other. For some applications, lens implant 10 further comprises anterior lens jointed elements 46, and levers 30 are in the jointed pivotable connection, at the respective first longitudinal sites 60 along levers 30, with anterior floating lens unit 24 by anterior lens jointed elements 46, respectively. Typically, anterior lens jointed elements 46 provide both rotational and radially flexibility between levers 30 and anterior floating lens unit 24. For some applications, anterior lens jointed elements 46 are oriented within 30 degrees of parallel to central optical axis 14, such as within 15 degrees of parallel, e.g., parallel. For some applications, anterior lens jointed elements 46 have a length of at least 0.5 mm, such as at least 0.9 mm; such relatively long lengths allow the use of a relatively small anterior lens 26, which may help facilitate placement of first anterior component 20 is an introducer tube, such as described hereinbelow with reference to FIGS. 8A-D.

For some applications, circumferential rim 48 is arranged in pivotable contact, such as in non-jointed pivotable contact, with posterior lens unit 50 when lens implant 10 is in the assembled state, such as shown in FIGS. 1A-C, 2A-C, 3B, and 4A-B. For some applications, circumferential rim 48 is arranged in the pivotable contact, such as in the non jointed pivotable contact, with posterior lens unit 50 around an entire circumference of circumferential rim 48 when lens implant 10 is in the assembled state, such as shown in FIGS. 1A-C, 2A-C, 3B, and 4A-B. Alternatively, circumferential rim 48 is arranged such that it does not contact posterior lens unit 50 at one or more circumferential locations of the circumferential rim.

For some applications, one or more portions of the material of lens implant 10 defines both levers 30 and circumferential rim 48, because the portions serve functionally as both levers 30 and circumferential rim 48. Typically, at least for these applications, levers 30 are integral with circumferential rim 48.

For some applications, circumferential rim 48 and posterior lens unit 50 are not shaped to provide a snapping interface therebetween. Not providing a snapping interface generally allows for easier in situ assembly of circumferential rim 48 and posterior lens unit 50, which naturally become assembled because of the constraints of capsular bag 12, with gentle prodding by the surgeon if necessary.

Typically, levers 30 and anterior rim 44 are not shaped to provide a snapping interface therebetween.

For some applications, levers 30 are shaped so as to define respective indentations 81 on respective anterior sides 82 at respective second longitudinal sites 62 (labeled in FIGS. 5A-B), and anterior rim 44 pivotably contacts (e.g., makes non-jointed pivotable contact with) the respective indentations 81 when lens implant 10 is in the assembled state.

For some applications, lens implant 10 is arranged when in the assembled state such that less than 10% (e.g., less than 5%, such as none) of the elastic potential energy in aggregate is stored at one or more interfaces between circumferential rim 48 and posterior lens unit 50, and in posterior lens unit 50, in aggregate (i.e., the sum of the elastic potential energy stored at one or more interfaces between circumferential rim 48 and posterior lens unit 50, and in posterior lens unit 50). This relatively low storage of elastic potential energy may be because, in some configurations, circumferential rim 48 is arranged in non-jointed pivotable contact with posterior lens unit 50 when lens implant 10 is in the assembled state, and posterior lens unit 50 does not materially bend or deform during accommodation of lens implant 10, but instead acts as a generally rigid body, such as described above.

Figure 6:
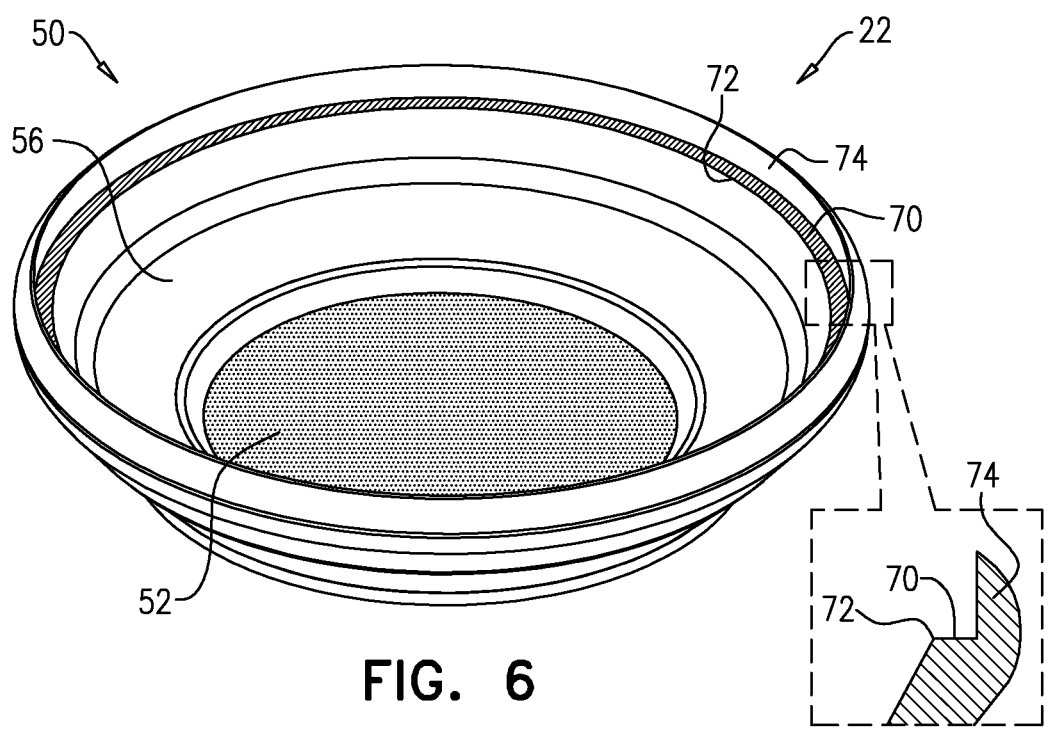
FIG. 6 is a schematic illustration of a posterior lens unit of the lens implant of FIGS. 1A-C, in accordance with an application of the present invention.

Reference is now made to FIGS. 4A-B, and additionally to FIG. 6, which is a schematic illustration of posterior lens unit 50, in accordance with an application of the present invention. For some applications, when lens implant 10 is in the assembled state, posterior lens unit 50 (e.g., posterior lens rim 56 thereof, described hereinbelow) is shaped so as to define one or more ledges 70 that face anteriorly (although they may also face radially inward or radially outward, while still facing anteriorly) and levers 30 are in the pivotable contact with the one or more ledges 70 at the respective third longitudinal sites 64 along levers 30, as shown in FIGS. 4A-B. For some applications, as shown, posterior lens unit 50 is shaped so as to define a single ledge 70 that extends around an entire circumference of posterior lens unit 50. For some applications in which circumferential rim 48 is arranged in the pivotable contact with posterior lens unit 50, circumferential rim 48 is in pivotable contact with the one or more ledges 70. As used in the present application, including in the claims, a "ledge" is a narrow surface that projects from another surface.

Typically, the one or more ledges 70 define one or more respective radially-inward edges 72 (which are typically sharp or curved), and levers 30 are in pivotable contact with the one or more radially-inward edges 72 at the respective third longitudinal sites 64 along levers 30 when lens implant 10 is in the assembled state. For applications in which posterior lens unit 50 is shaped so as to define single ledge 70 that extends around the entire circumference of posterior lens unit 50, the single ledge 70 typically defines exactly one radially-inward edge 72, with which levers 30 are in pivotable contact. For some applications in which circumferential rim 48 is arranged in the pivotable contact with posterior lens unit 50, circumferential rim 48 is in pivotable contact with the one or more radially-inward edges 72. The relative thickness of circumferential rim 48 may allow the circumferential rim to reliably pivot around the one or more radially-inward edges 72.

Typically, posterior lens unit 50 is shaped so as to define a circumferential lip 74 that extends anteriorly beyond the one or more ledges 70, and the one or more ledges 70 project from circumferential lip 74 radially inward toward central optical axis 14. Lip 74 generally helps the surgeon assemble circumferential rim 48 and posterior lens unit 50 in situ, and may also help hold circumferential rim 48 and posterior lens unit 50 together after assembly.

Figure 7:
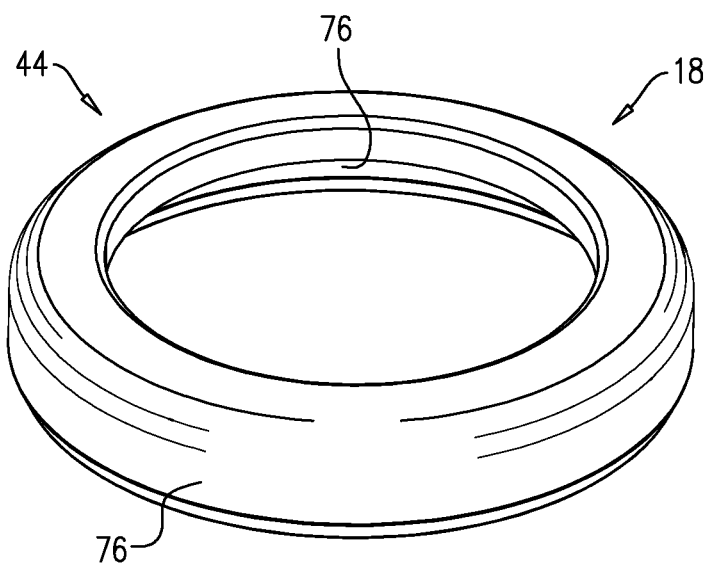
FIG. 7 is a schematic illustration of an anterior rim of the lens implant of FIGS. 1A-C, in accordance with an application of the present invention.

Reference is still made to FIGS. 4A-B, and is additionally made to FIG. 7, which is a schematic illustration of anterior rim 44, in accordance with an application of the present invention. For some applications, anterior rim 44 is shaped so as to define a posteriorly-extending connection portion 76, which typically extends around an entire circumference of anterior rim 44. Levers 30 are in pivotable contact (e.g., non-jointed pivotable contact) with posteriorly-extending connection portion 76 at respective second longitudinal sites 62 along levers 30. For some applications, levers 30 are in jointed pivotable contact with anterior rim 44 (configuration not shown).

Reference is again made to FIGS. 4A-B. For some applications, a radially-outer perimeter 124 of lens implant 10 is defined by posterior lens unit 50. For some applications, for each of levers 30:

(a) a line defined by second longitudinal site 62 of lever 30 and third longitudinal site 64 of lever 30, if projected onto a plane defined by radially-outer perimeter 124 of lens implant 10, and (b) a line tangential to radially-outer perimeter 124 of lens implant 10 at a circumferential site of perimeter 124 circumferentially corresponding to third longitudinal site 64 of lever 30, form an angle of between 75 and 105 degrees, such as between 85 and 95 degrees, e.g., 90 degrees, and second longitudinal site 62 is longitudinally between first longitudinal site 60 and third longitudinal site 64 along lever 30, such that third longitudinal site 64 serves as a fulcrum 66 for lever 30.

Alternatively or additionally, for some applications, for each of levers 30:

(a) a line defined by first longitudinal site 60 of lever 30 and third longitudinal site 64 of lever 30, if projected onto a plane defined by radially-outer perimeter 124 of lens implant 10, and (b) a line tangential to radially-outer perimeter 124 of lens implant 10 at a circumferential site of perimeter 124 circumferentially corresponding to third longitudinal site 64 of lever 30, form an angle of between 75 and 105 degrees, such as between 85 and 95 degrees, e.g., 90 degrees, and second longitudinal site 62 is longitudinally between first longitudinal site 60 and third longitudinal site 64 along lever 30, such that third longitudinal site 64 serves as a fulcrum 66 for lever 30.

Reference is made to FIG. 3A. For some applications, lens implant 10 comprises:

a first posterior component 28, which comprises posterior lens unit 50, which comprises posterior lens 52;

a second posterior component 22, which comprises a posterior lens rim 56;

a first anterior component 20, which comprises (a) anterior floating lens unit 24, which comprises anterior lens 26, and (b) levers 30; and a second anterior component 18, which comprises anterior rim 44.

Typically, first posterior component 28, second posterior component 22, first anterior component 20, and second anterior component 18 are not integral with one another, and are shaped so as to be assemblable into the assembled state in situ with one another in capsular bag 12 of the human eye.

As described hereinbelow with reference to FIG. 9G, posterior lens 52 and posterior lens rim 56 are shaped so as to be assemblable together in situ in capsular bag 12 of a human eye such that posterior lens rim 56 radially surrounds at least an axial portion 59 of posterior lens 52 (labeled in FIG. 4A).

Typically, first posterior component 28 comprises exactly one polymeric piece, which is shaped so as to define posterior lens unit 50. Typically, second posterior component 22 comprises exactly one polymeric piece, which is shaped so as to define posterior lens rim 56. Typically, first anterior component 20 comprises exactly one polymeric piece, which is shaped so as to define anterior floating lens unit 24 and levers 30. Typically, second anterior component 18 comprises exactly one polymeric piece, which is shaped so as to define anterior rim 44.

For some applications, posterior lens 52 (or all of first posterior component 28) comprises optical acrylic, which is typically flexible, and may be either hydrophobic or hydrophilic. For some applications, posterior lens rim 56 (or all of second posterior component 22) and/or anterior rim 44 (or all of second anterior component 18) comprise silicone, typically with a hardness 50-80 Shore A, such as 70-80 Shore A. For some applications, anterior lens 26 (or all of anterior floating lens unit 24) and/or levers 30 (or all of first anterior component 20) comprises optical silicone, typically having a refractive index of 1.43 to 1.46, and/or a hardness of 40-50 Shore A.

Posterior lens unit 50 remains generally motionless with respect to the posterior portion of natural capsular bag 12 of the eye during accommodation of lens implant 10. Lens implant 10 is configured such that anterior floating lens unit 24 moves with respect to posterior lens unit 50 in response to the natural accommodation mechanism of the eye. The natural accommodation mechanism of the eye changes the shape of natural capsular bag 12, as shown in FIGS. 2A-C. In the fully-unaccommodated state shown in FIG. 2A, the ciliary muscle is relaxed and the zonular fibers are therefore tensed, causing the capsular bag to assume a relatively narrow width (in an anterior-posterior direction) and relatively large diameter. Thus shaped, the capsular bag squeezes lens implant 10 in the anterior-posterior direction. In contrast, in the fully-accommodated state shown in FIG. 2C, the ciliary muscle contracts, thereby releasing the tension of the zonular fibers on the capsular bag, causing the capsular bag to assume a relatively large width and relative small diameter. This shape of the capsular bag allows lens implant 10 to expand in the anterior-posterior direction. (As used herein, the diameter of the capsular bag means the greatest diameter of the capsular bag when viewed from its posterior aspect.)

Anterior rim 44 is disposed such that anterior floating lens unit 24 is movable toward and away from anterior rim 44, in the anterior-posterior direction. As the width (in the anterior-posterior direction) of the capsular bag changes, anterior rim 44 moves with respect to posterior lens unit 50, thereby changing the distance therebetween.

As mentioned above, anterior floating lens unit 24 comprises anterior lens 26, and posterior lens unit 50 comprises posterior lens 52. Each of lens units 24 and 50 may comprise one or more additional optical elements, such as additional lenses (e.g., convex lenses, concave lenses, biconvex lenses, biconcave lenses, spherical lenses, aspheric lenses, and/or astigmatic lenses), fixed power optics, deformable optics, aberration free optics, doublets, triplets, filtered optics, or combinations of these lenses, as is known in the optical arts. For some applications, anterior lens 26 is the only optical element of anterior floating lens unit 24, and/or posterior lens 52 is the only optical element of posterior lens unit 50. For some applications, one or more of lens units 24 and 50 are attached to the implant during manufacture. Alternatively or additionally, one or more of the lens units may be attached by a healthcare worker either prior to or during the implantation procedure, such as to provide the lens unit most appropriate for the particular patient.

As used in the present application, including in the claims, a "lever" is a beam that is used to move an object at a first point by a force applied at a second point, and that pivots about a fulcrum at a third point. Typically, for each respective lever 30 of levers 30, second longitudinal site 62 is longitudinally between first longitudinal site 60 and third longitudinal site 64 along the respective lever 30, such that third longitudinal site 64 serves as a fulcrum 66 for respective lever 30. Thus, first longitudinal site 60, second longitudinal site 62, and third longitudinal site 64 correspond with the first, second, and third points, respectively, in the definition above.

Force is applied to second longitudinal site 62 by anterior rim 44, and, as a result, first longitudinal site 60 (and anterior floating lens unit 24) moves more than an anterior-posterior distance that second longitudinal site 62 (and anterior rim 44) moves, typically between 1.5 and 4 times the anterior-posterior distance that second longitudinal site 62 (and anterior rim 44) moves. For some applications, a distance between second and third longitudinal sites 62 and 64 is between 0.8 and 1.6 mm, and a distance between first and third longitudinal sites 60 and 64 is between 1.2 and 2.4 mm, providing a gain of between 1.5 and 4. Typically, second longitudinal sites 62 are disposed radially inward from third longitudinal sites 64, respectively. Typically, first longitudinal sites 60 are disposed radially inward from second longitudinal sites 62 and third longitudinal sites 64, respectively.

Levers 30 are thus configured to magnify the relatively small change in the distance between anterior rim 44 and posterior lens unit 50, in order to move anterior floating lens unit 24 by a greater distance with respect to posterior lens unit 50. In other words, lens implant 10 is configured such that levers 30 move anterior floating lens unit 24 by a first anterior-posterior distance with respect to posterior lens unit 50 when anterior rim 44 moves a second anterior-posterior distance with respect to posterior lens unit 50, which first distance is greater than the second distance. Because of this distance magnification, lens implant 10 provides a high level of accommodation that mimics that of the natural eye. Typically, the first distance is at least 1.4 times the second distance, i.e., the lever provides a gain of at least 1.4. For example, the first distance may be at least 1.5 (e.g., at least 1.8, such as between 1.8 and 3) times the second distance.

The anterior and posterior movement of anterior floating lens unit 24 changes the distance between the anterior and posterior lens units, thereby adjusting the focal length of lens implant 10. In the fully-accommodated state, which provides near vision, lens implant 10 is relatively wide (in the anterior-posterior direction), with a large separation between the anterior and posterior lens units, creating a large free space between the complexes. In the fully-unaccommodated state, which provides distance vision, the implant is relatively narrow, with a small separation between anterior and posterior complexes. Anterior floating lens unit 24 typically shifts at least 1 mm between the fully-unaccommodated and fully-accommodated states. Typical movement of the anterior lens relative to posterior lens 52 is between 0.5 and 2.0 mm, such as between 1 and 1.5 mm, as lens implant 10 transitions between the fully-unaccommodated and fully-accommodated states.

Anterior floating lens unit 24 moves within an interior space of lens implant 10, which is typically open to the natural fluid within the eye. The floating lens unit is configured to create minimum drag during movement, while maintaining the optical performance of the combined lens structure. For example, the floating lens unit may have a smooth shape, and/or may be coated with a hydrophobic coating such as silicone. Typically, the anterior and posterior lens units are configured to together create an optical structure having a total power that varies between +15 D and +25 D, as selected by the physician implanting lens implant 10.

To minimize posterior capsular opacification, posterior lens 52 is typically provided with a clearly-defined corner 99 (e.g., having an angle of 80-150 degrees, e.g., 90-120 degrees), at the junction of the posterior and lateral surfaces of posterior lens 52.

(As used in the present application, including in the claims, transitioning between the fully-accommodated and the fully-unaccommodated states is to be understood as meaning making a transition that begins at the fully-accommodated state and continues all the way to the fully-unaccommodated state, or vice versa.)

Reference is now made to FIGS. 8A-D, which are schematic illustrations of respective components of an introducer system 100, in accordance with an application of the present invention. Introducer system 100 may be used for implanting lens implant 10, described hereinabove with reference to FIGS. 1A-C, 2A-C, 3A-B, and 4A-B, in capsular bag 12 of a human eye.

Figure 8A:
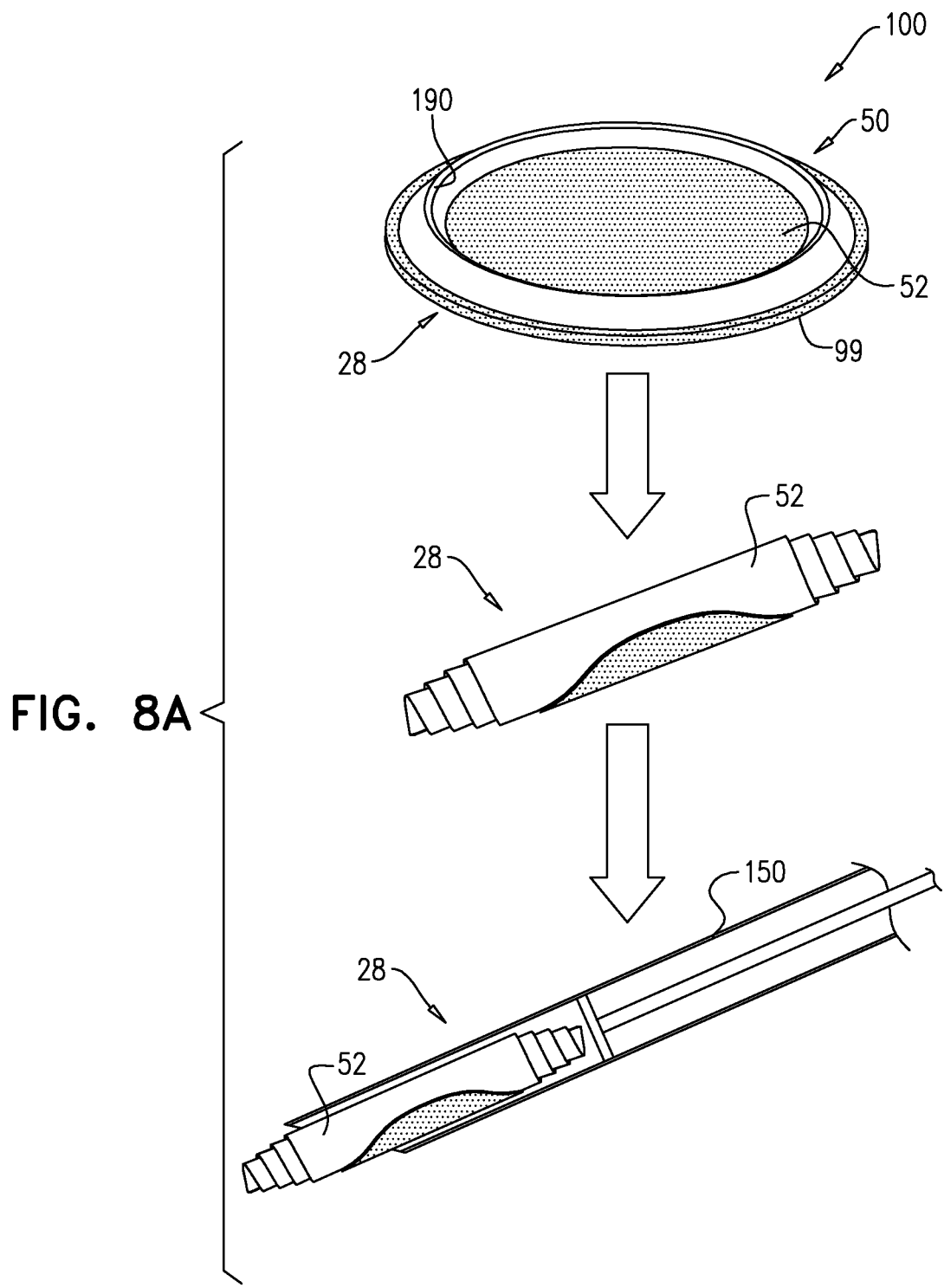
FIGS. 8A-D are schematic illustrations of respective components of an introducer system, in accordance with an application of the present invention.
Figure 8B:
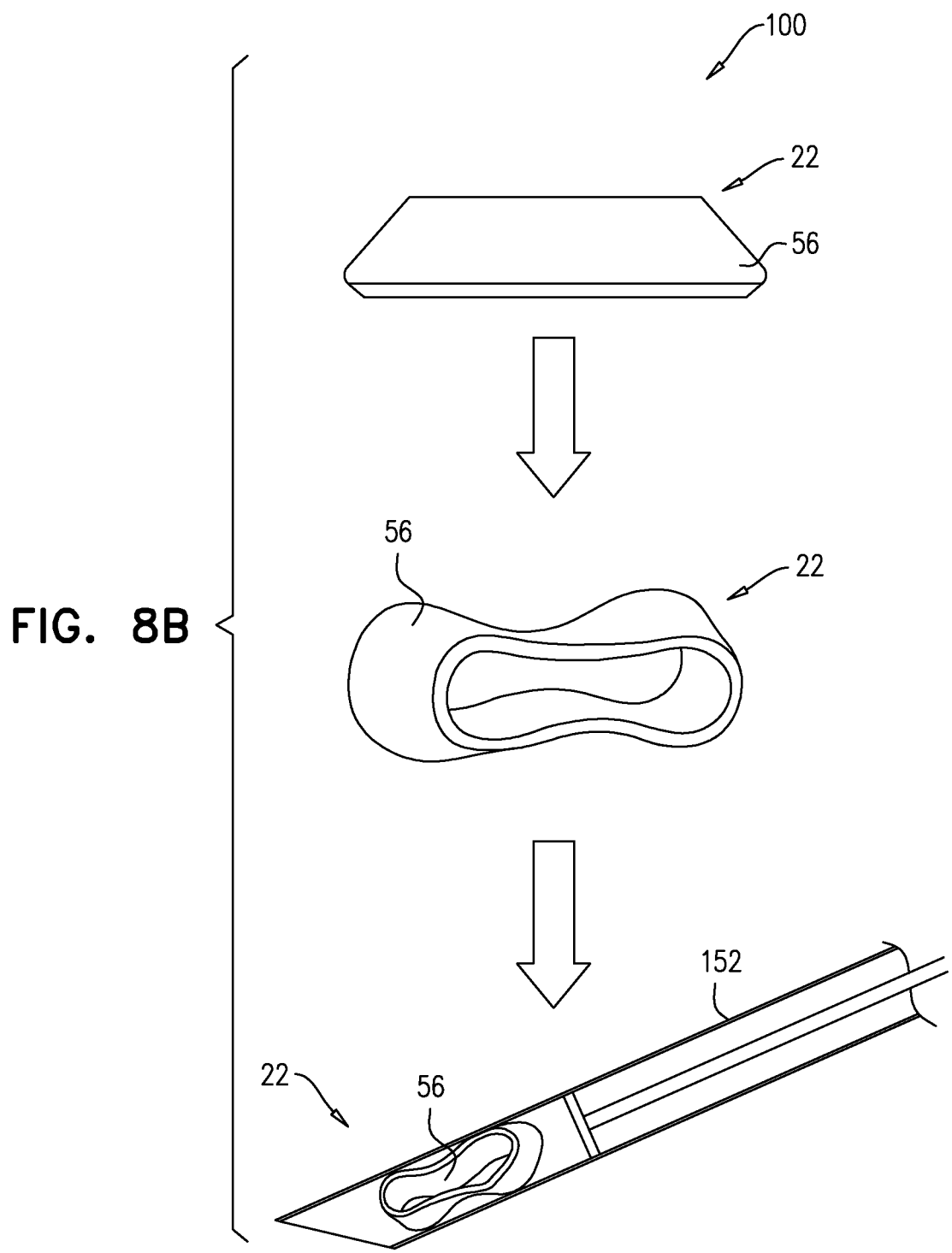
Figure 8C:
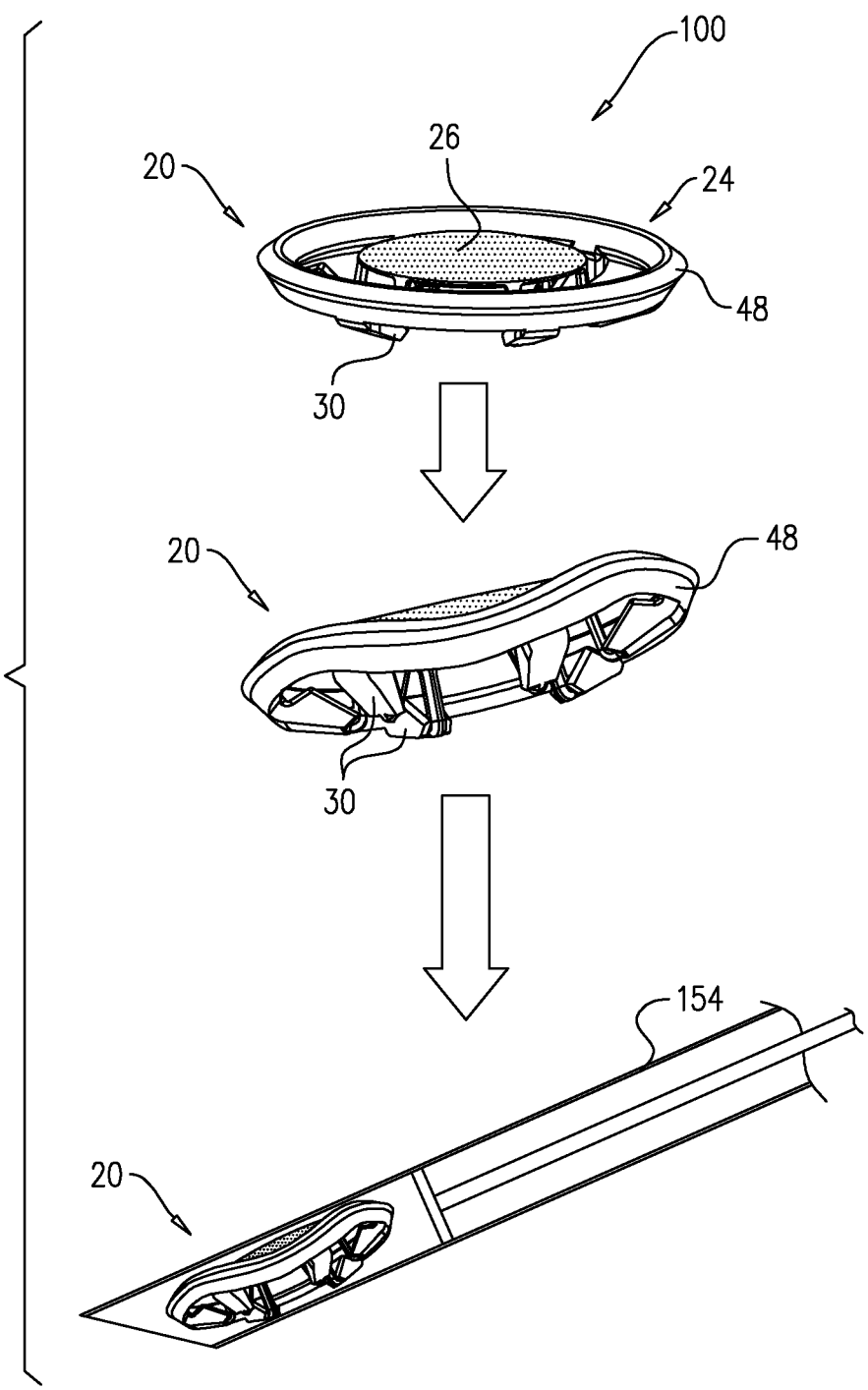
Figure 8D:
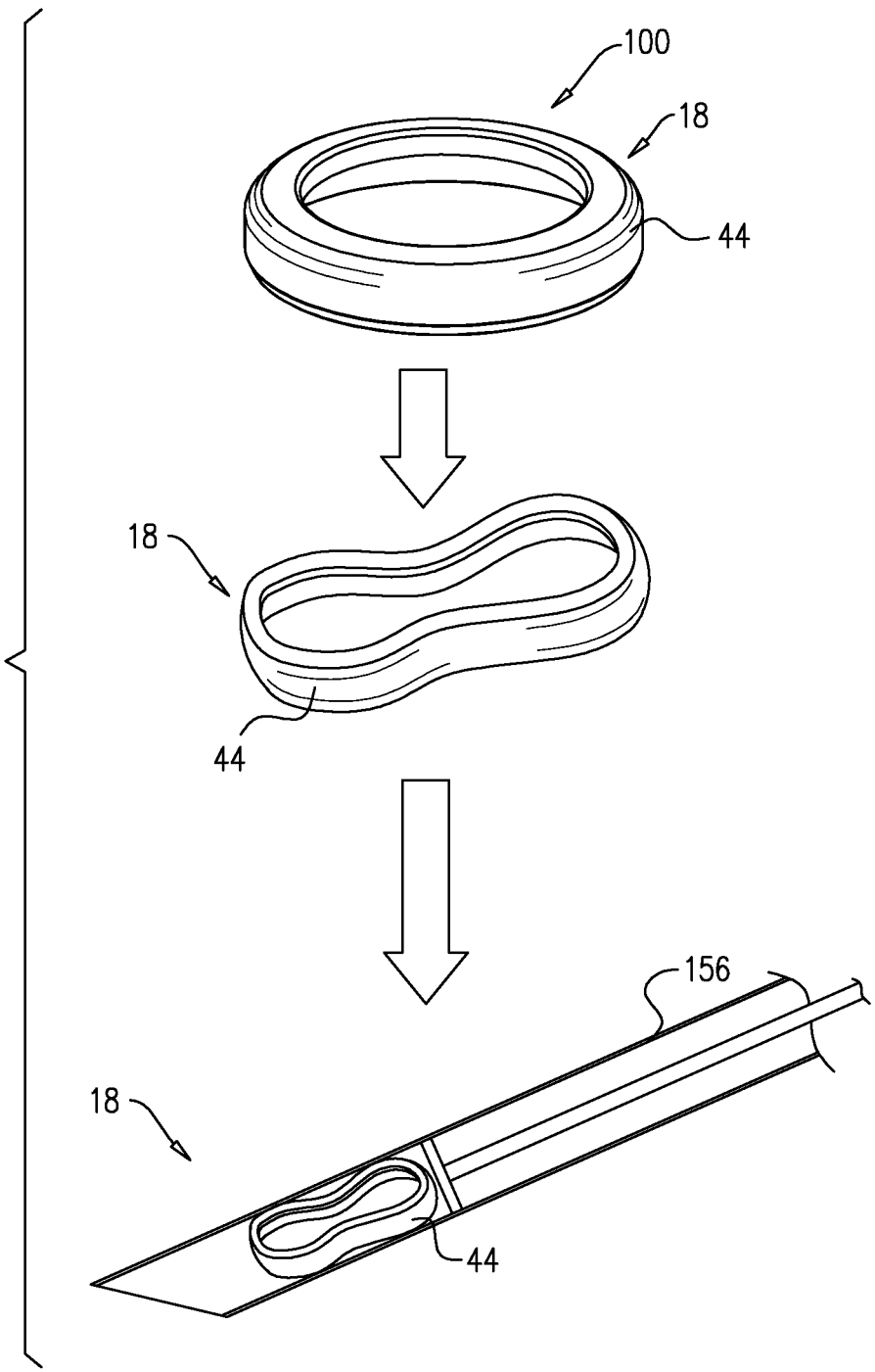

For some applications, introducer system 100 comprises one or more (e.g., all) of the following introducer tubes:

- a first posterior introducer tube 150, in which first posterior component 28 is removably disposed, for example while rolled, such as shown in FIG. 8A; FIG. 8A also shows the removable disposal of posterior lens 52 of first posterior component 28 in first posterior introducer tube 150;
- a second posterior introducer tube 152, in which second posterior component 22 is removably disposed, for example while folded, such as shown in FIG. 8B; FIG. 8B also shows the removable disposal of posterior lens rim 56 of second posterior component 22 in second posterior introducer tube 152;
- a first anterior introducer tube 154, in which first anterior component 20 is removably disposed, for example while folded, such as shown in FIG. 8C; FIG. 8C also shows the removal disposal of anterior floating lens unit 24 (which comprises anterior lens 26) and levers 30 of first anterior component 20 in first anterior introducer tube 154; and
- a second anterior introducer tube 156, in which second anterior component 18 is removably disposed, for example while folded, such as shown in FIG. 8D; FIG. 8D also shows the removal disposal of anterior rim 44 of second anterior component 18 in second anterior introducer tube 156.

For some applications, first posterior introducer tube 150, second posterior introducer tube 152, first anterior introducer tube 154, and second anterior introducer tube 156 are distinct and separate from each other.

Typically, each of first posterior introducer tube 150, second posterior introducer tube 152, first anterior introducer tube 154, and second anterior introducer tube 156 has an outer diameter of no more than 3 mm, such as no more than 2.5 mm, e.g., no more than 2 mm. This outer diameter allows the introducer tubes to be inserted into the eye through a 2-3 mm incision. By contrast, implantation of some accommodating intraocular lenses (AIOLs) requires an incision of 4-6 mm, which may cause astigmatism and/or other complications.

Reference is made to FIGS. 9A-L, which are schematic illustrations of a method of implanting intraocular lens implant 10, in accordance with an application of the present invention. This four-step insertion procedure generally allows the use of a smaller incision than is necessary for a one-step insertion procedure of a single-piece implant. Typically, upon assembly, all of the rims and lenses of lens implant 10 are concentric about central optical axis 14.

Figure 9A:
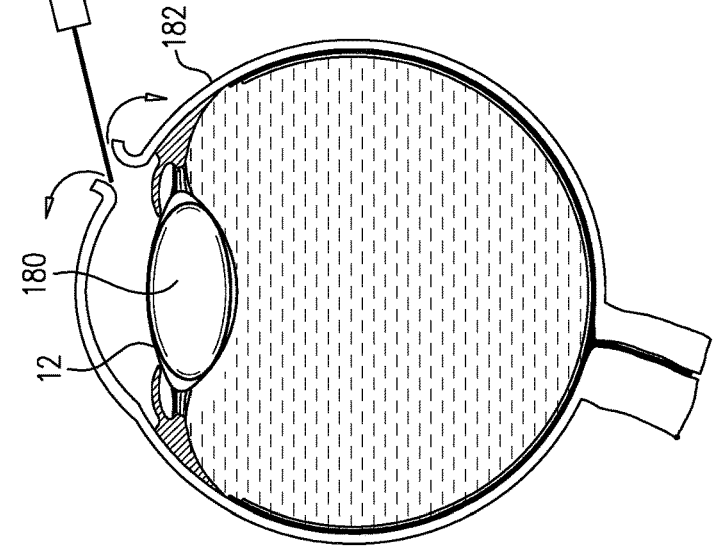
FIGS. 9A-L are schematic illustrations of a method of implanting the lens implant of FIGS. 1A-C, in accordance with an application of the present invention.
Figure 9B:
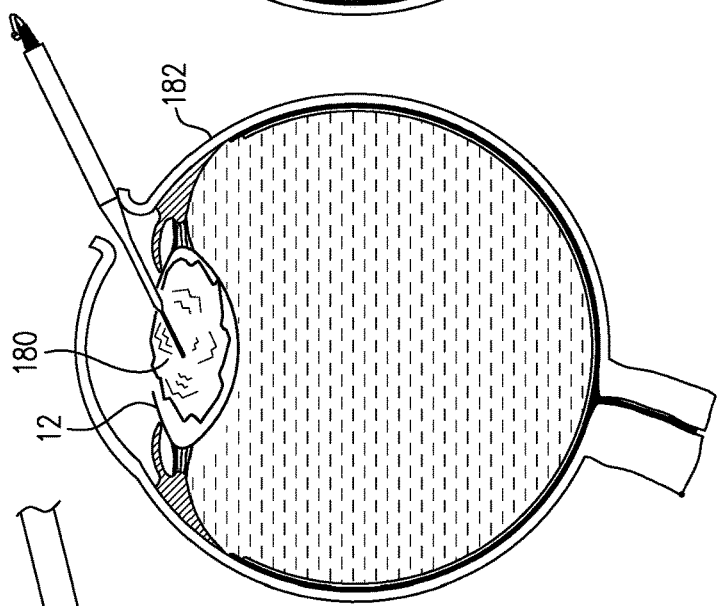
Figure 9C:
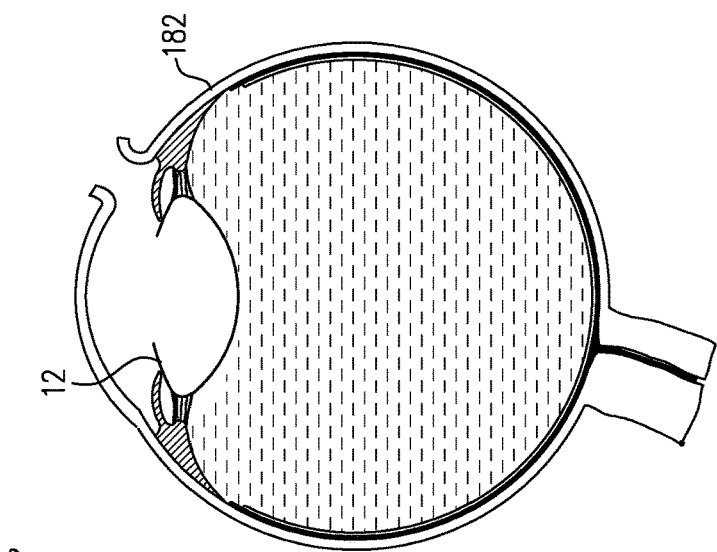

As shown in FIGS. 9A-C, a natural lens 180 is removed from a human eye 182, such as using conventional techniques known in the art. For example, as shown in FIG. 9B, an anterior capsulectomy may be made using continuous curvilinear capsulorhexis (CCC).

Figure 9D:
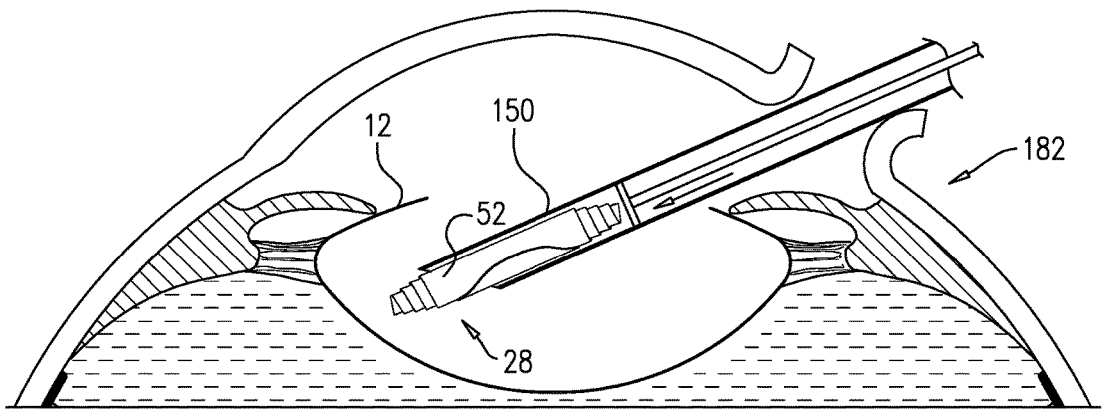
Figure 9E:
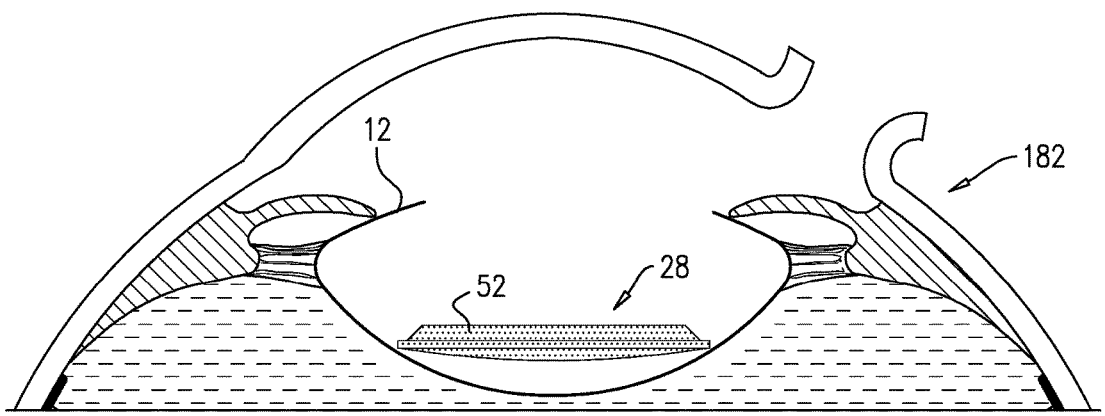

As shown in FIGS. 9D-E, first posterior introducer tube 150 is inserted into capsular bag 12 of eye 182, and first posterior component 28 (which comprises posterior lens 52) is released from the introducer tube in capsular bag 12, is allowed to unroll, for example, and positioned posteriorly in capsular bag 12.

Figure 9F:
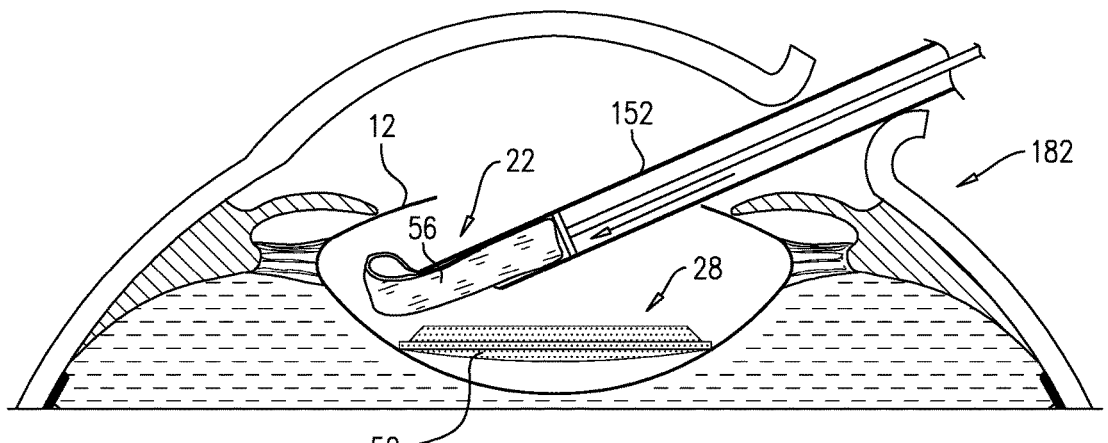
Figure 9G:
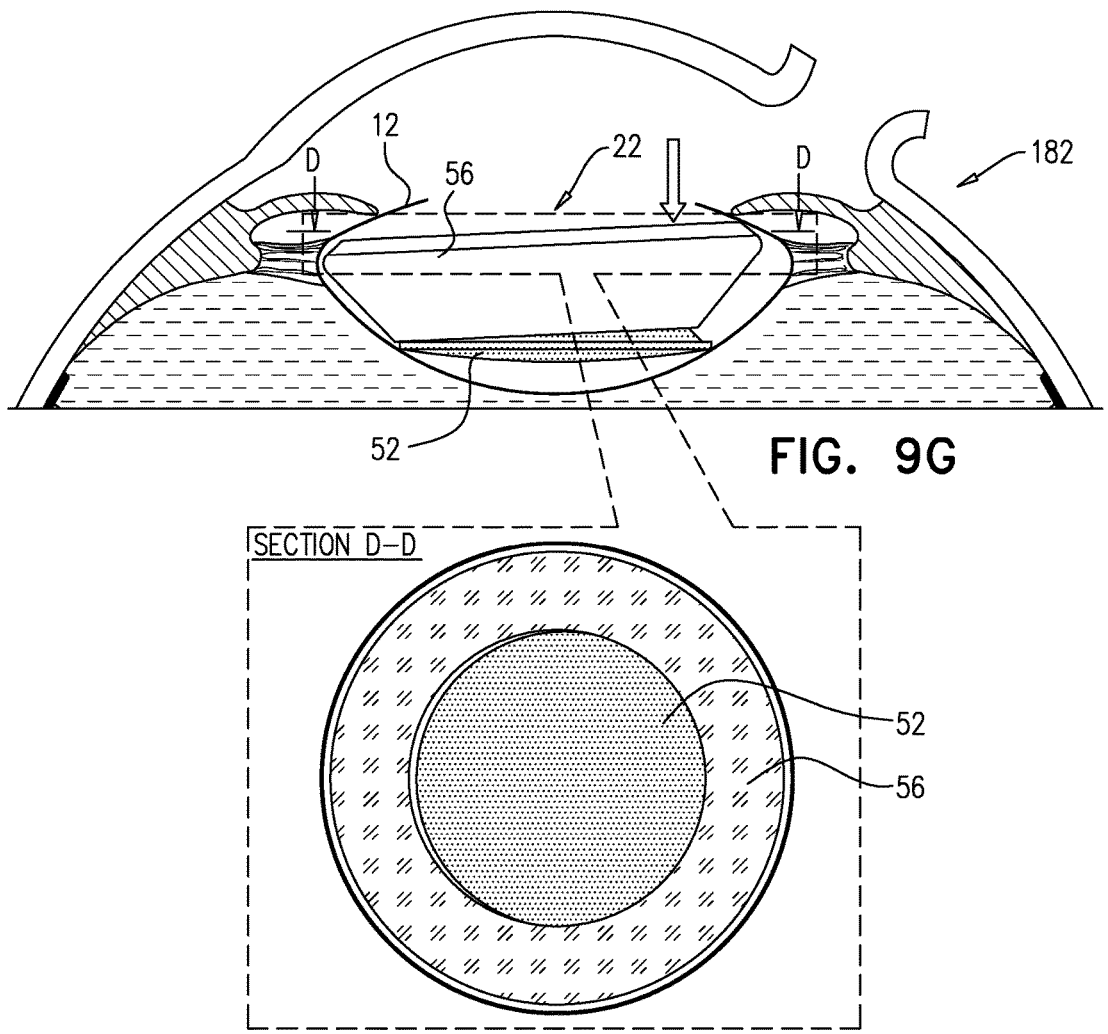
Figure 9H:
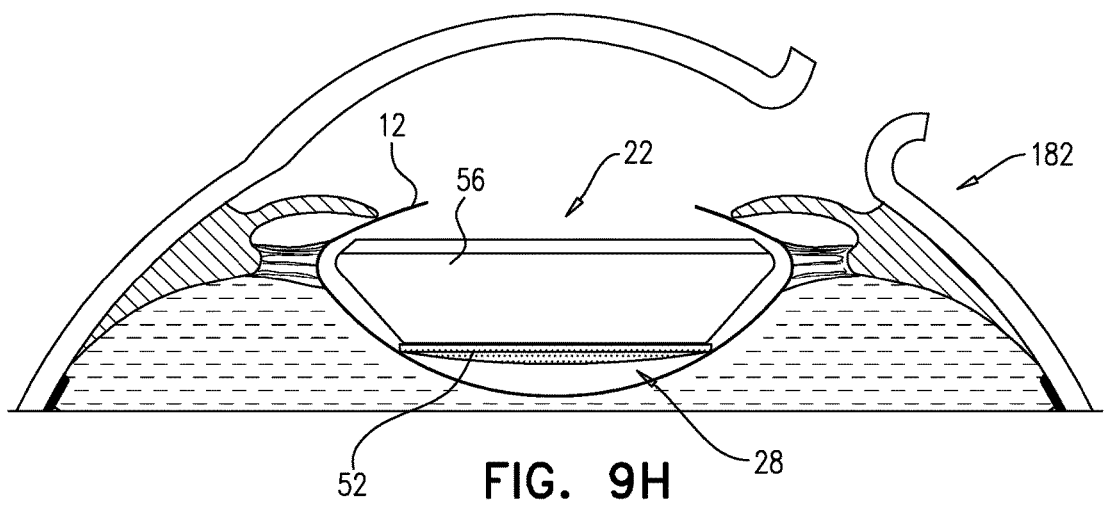

As shown in FIGS. 9F-H, second posterior introducer tube 152 is inserted into capsular bag 12 of eye 182, and posterior lens rim 56 of second posterior component 22 is released from the introducer tube in capsular bag 12, is allowed to unfold, for example, in capsular bag 12, and is assembled in situ with first posterior component 28, such that posterior lens rim 56 radially surrounds at least axial portion 59 of posterior lens 52, as shown in FIG. 9G. For some applications, first and second posterior components 28 and 22 have matching beveled edges; second posterior component 22 is moved with respect to first posterior component 28 until the components align and become coupled together. For some applications, posterior lens 52 is shaped so as to define an axially-directed ledge 190 (labeled in FIG. 8A), which the surgeon can use to manipulate posterior lens 52 with respect to posterior lens rim 56 if necessary to couple the lens to the rim.

For some applications (configuration not shown), posterior lens rim 56 is introduced into capsular bag 12 folded or rolled, without being removably disposed in an introducer tube.

The scope of the present invention includes performing the steps of the method described with reference to FIGS. 9F-H before performing the steps of the method described with reference to FIGS. 9D-E.

Figure 9I:
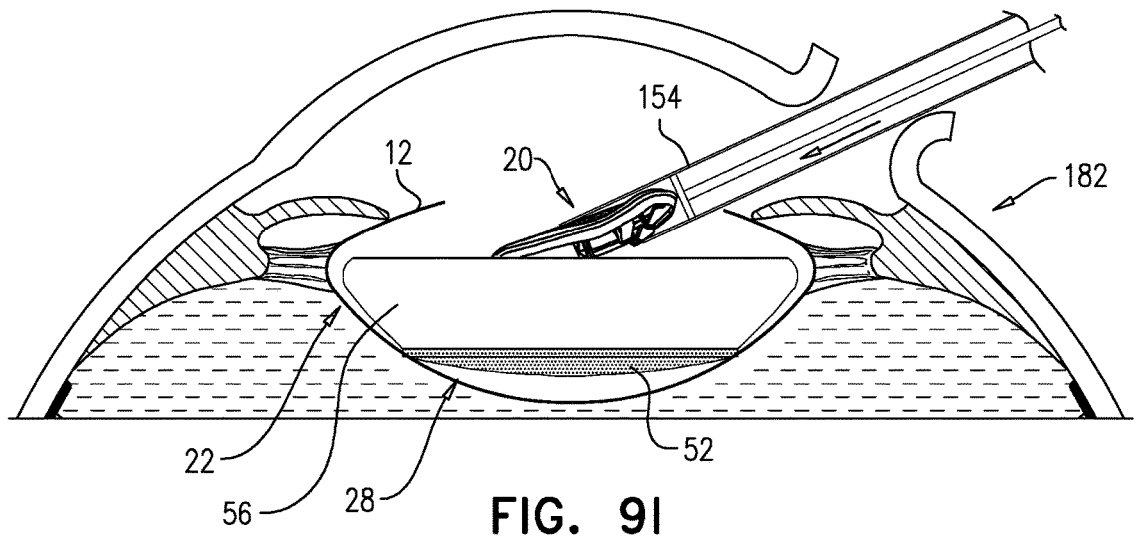
Figure 9J:
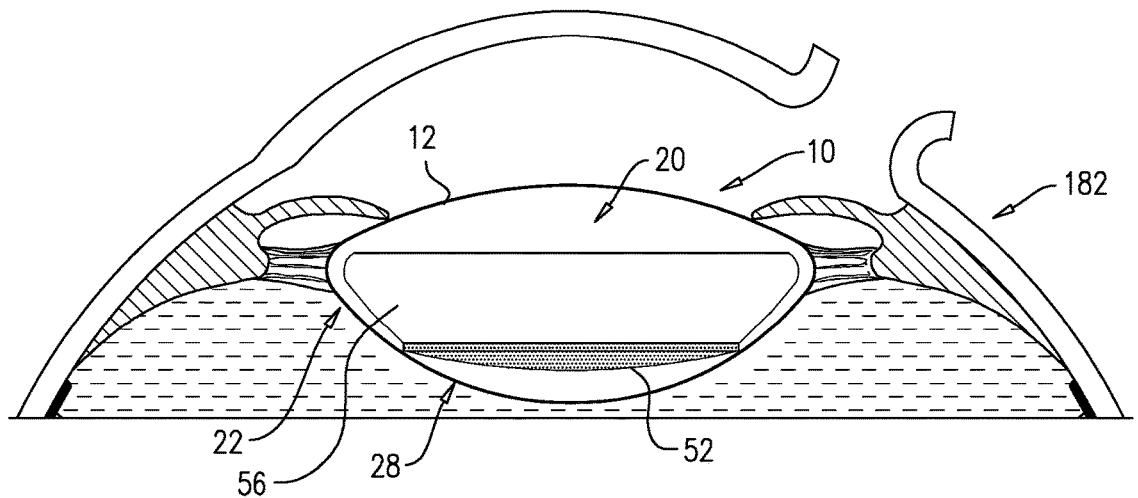

As shown in FIGS. 9I-J, after first and second posterior components 28 and 22 have been released into capsular bag 12, first anterior introducer tube 154 is inserted into capsular bag 12 of eye 182, and first anterior component 20, including anterior lens 26 of anterior floating lens unit 24, is released from the introducer tube in capsular bag 12. Anterior floating lens unit 24 is coupled to posterior lens rim 56, as shown in FIG. 9J.

Figure 9K:
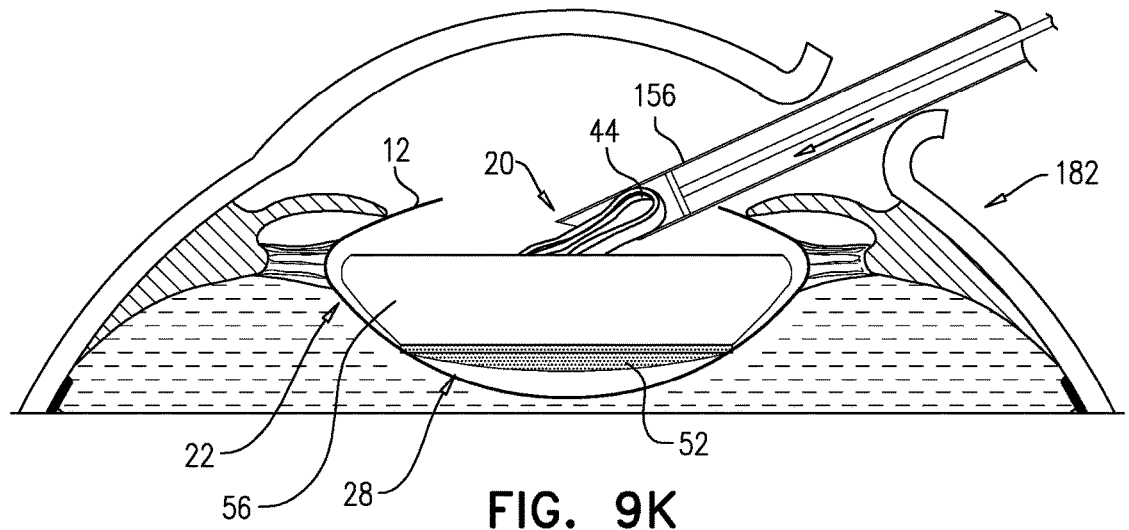
Figure 9L:
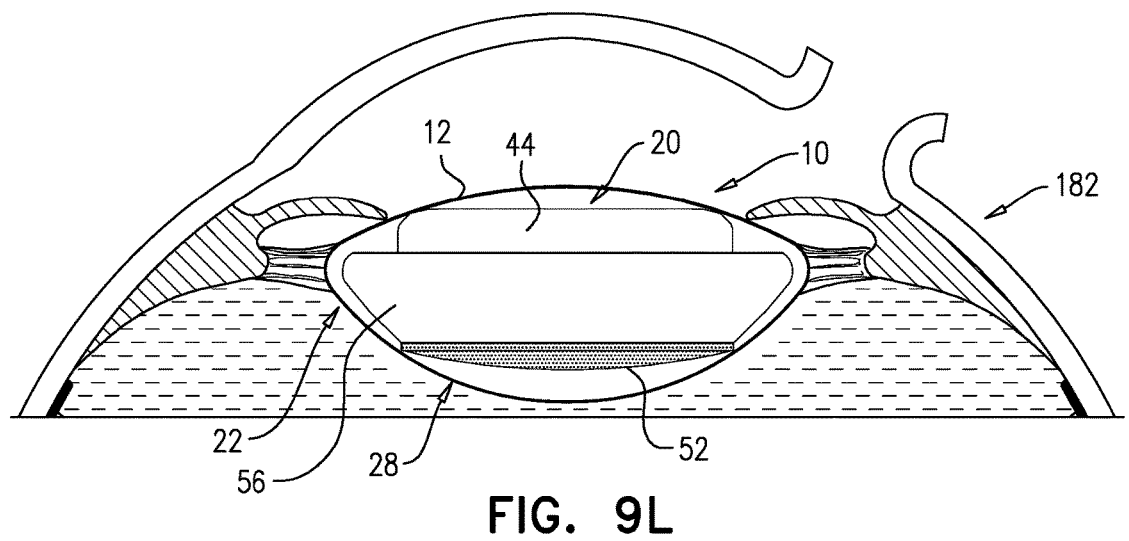

As shown in FIGS. 9K-L, after first and second posterior components 28 and 22 and first anterior component 20 have been released into capsular bag 12, second anterior introducer tube 156 is inserted into capsular bag 12 of eye 182, and second anterior component 18, including anterior rim 44, is released from the introducer tube in capsular bag 12. Anterior rim 44 is assembled with levers 30, as shown in FIG. 9L, thereby completing the implantation procedure.

For some applications, a single introducer tube is used to introduce all of the components of lens implant 10. Alternatively, for some applications, exactly two introducer tubes are used to introduce all of the components of lens implant 10, i.e., two of the components described above are introduced in a first introducer tube, and the other two components are introduced in a second introducer tube, or three of the components described above are introduced in a first introducer tube, and the other component is introduced in a second introducer tube. Alternatively, for some applications, exactly three introducer tubes are used to introduce all of the components of lens implant 10, i.e., one of the components described above is introduced in a first introducer tube, another one of the components is introduced in a second introducer tube, and the remaining two components are introduced in a third introducer tube. The one or more introducer tubes may have the outer diameters described hereinabove with reference to FIGS. 8A-D regarding first posterior introducer tube 150, second posterior introducer tube 152, first anterior introducer tube 154, and second anterior introducer tube 156. Typically, first posterior component 28, second posterior component 22, first anterior component 20, and second anterior component 18 are removably disposed at respective axial positions that do not axially overlap with one another (either in the same introducer tube, if two or more components are disposed in a single introducer tube, or because the components are disposed in separate introducer tubes).

For some applications, posterior lens 52 is inserted into capsular bag 12 after posterior lens rim 56 is released from second posterior introducer tube 152 in capsular bag 12. Alternatively, posterior lens 52 is inserted into capsular bag 12 before posterior lens rim 56 is released from second posterior introducer tube 152 in capsular bag 12.

As appropriate, lens implant 10 may partially or wholly comprise silicone, or lens implant 10 may partially or wholly comprise flexible acrylic. For some applications, a portion of lens implant 10 comprises silicone and another portion of lens implant 10 comprises flexible acrylic (optionally, lens implant 10 consists essentially entirely of silicone and acrylic).

Reference is now made to FIGS. 1A-9L. For some applications, as shown in the figures, lens implant 10 does not comprise any haptics.

Although lens implant 10 has been described herein as being assemblable in situ in the eye, for some application, one or more (e.g., all) of the components of lens implant 10 described herein are assembled before implantation, either during manufacture and/or during the implantation procedure.

Although the four-part design of lens implant 10 has been described as being use for an accommodating IOL, the four-part design may also be used in non-accommodating and single lenses as well.

As used in the present application, including in the claims, "axial" means a direction along central optical axis 14 of lens implant 10. As used in the present application, including in the claims. "radial" means in a direction toward or away from central optical axis 14 of lens implant 10. (Although transparent, anterior lens 26 and posterior lens 52 are shaded in the figures for clarity of illustration; the lenses may comprise the same material as some or all the other components of lens implant 10.)

The scope of the present invention includes embodiments described in the following applications and publications, which are assigned to the assignee of the present application and are incorporated herein by reference. In an embodiment, techniques and apparatus described in one or more of the following applications and publications are combined with techniques and apparatus described herein:

US Patent Application Publication 2011/0071628;
U.S. Provisional Application 61/745,851, filed Dec. 26, 2012;
US Patent Application Publication 2014/0180407;
US Patent Application Publication 2014/0309735;
U.S. Provisional Application 62/017,232, filed Jun. 25, 2014;
International Publication WO 2015/198236;
U.S. application Ser. No. 15/170,417, filed Jun. 1, 2016, which published as U.S. Patent Application Publication 2017/0348094; and
U.S. Provisional Application 62/439,992, filed Dec. 29, 2016, entitled, "Accommodative intraocular lens."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus comprising an accommodating intraocular lens implant, which is shaped so as to be assemblable into an assembled state in situ in a capsular bag of a human eye so as to have a central optical axis, and which comprises:
   an anterior floating lens unit, which comprises an anterior lens;
   a posterior lens unit, which comprises a posterior lens;
   an anterior rim;
   levers, which are, when the lens implant is in the assembled state, (a) (i) in pivotable contact with the anterior floating lens unit at respective first longitudinal sites along the levers, (ii) in pivotable contact with the anterior rim at respective second longitudinal sites along the levers, and (iii) in pivotable contact with the posterior lens unit at respective third longitudinal sites along the levers, and (b) arranged to move the anterior floating lens unit toward and away from the anterior rim, in an anterior-posterior direction, wherein, for each respective lever of the levers, the second longitudinal site is farther from the central optical axis than the first longitudinal site is from the central optical axis, and the third longitudinal site is farther from the central optical axis than the second longitudinal site is from the central optical axis; and
   a circumferential rim, which is attached to the levers such that at least a portion of the circumferential rim is farther from the central optical axis than the second longitudinal sites are from the central optical axis,
   wherein the lens implant is arranged such that in the assembled state:
      elastic potential energy is stored in the lens implant as a result of deformation of the lens implant during a transition from a fully-accommodated state to a fully-unaccommodated state,
      at least 50% of the elastic potential energy stored in the lens implant as the result of the deformation is stored in the circumferential rim, a surface defined by the circumferential rim faces at least partially anteriorly when the lens implant is in the fully-accommodated state, and the surface rotates toward the central optical axis during the transition from the fully-accommodated state to the fully-unaccommodated state.

2. The apparatus according to claim 1, wherein the lens implant is arranged when in the assembled state such that at least 70% of the elastic potential energy stored in the lens implant as the result of the deformation is stored in the circumferential rim.

3. The apparatus according to claim 2, wherein the lens implant is arranged when in the assembled state such that at least 90% of the elastic potential energy stored in the lens implant as the result of the deformation is stored in the circumferential rim.

4. The apparatus according to claim 1, wherein the lens implant is arranged when in the assembled state such that less than 10% of the elastic potential energy in aggregate is stored in the levers at the second longitudinal sites, at respective interfaces between the levers and the anterior rim, and in the anterior rim, in aggregate.

5. The apparatus according to claim 1, wherein the lens implant is arranged when in the assembled state such that less than 10% of the elastic potential energy in aggregate is stored at respective interfaces between the levers and the posterior lens unit, and in the posterior lens unit, in aggregate.

6. The apparatus according to claim 1, wherein the levers, when the lens implant is in the assembled state, are in non-jointed pivotable contact with the anterior rim at the respective second longitudinal sites along the levers.

7. The apparatus according to claim 1, wherein the levers, when the lens implant is in the assembled state, are in non-jointed pivotable contact with the posterior lens unit at the respective third longitudinal sites along the levers.

8. The apparatus according to claim 1, wherein the levers, when the lens implant is in the assembled state, are in jointed pivotable connection with the anterior floating lens unit at the respective first longitudinal sites along the levers.

9. The apparatus according to claim 8,
wherein the lens implant further comprises anterior lens jointed elements, and
wherein the levers are in the jointed pivotable connection, at the respective first longitudinal sites along the levers, with the anterior floating lens unit by the anterior lens jointed elements, respectively.

10. The apparatus according to claim 9, wherein the lens implant is arranged when in the assembled state such that less of the elastic potential energy in aggregate is stored (a) in the levers at the second longitudinal sites, at respective interfaces between the levers and the anterior rim, and in the anterior rim, in aggregate than (b) in the levers at the first longitudinal sites, at respective interfaces between the levers and the anterior floating lens unit, and in the anterior lens jointed elements, in aggregate.

11. The apparatus according to claim 1, wherein the levers and the anterior rim are not shaped to provide a snapping interface therebetween.

12. The apparatus according to claim 1, wherein the lens implant is arranged when in the assembled state such that at least 50% of the elastic potential energy stored in the lens implant as the result of the deformation is stored in a volume of the circumferential rim, the volume equal to at least 4 mm3.

13. The apparatus according to claim 1, wherein the lens implant is arranged when in the assembled state such that at least 50% of the elastic potential energy stored in the lens implant as the result of the deformation is stored in a volume of the circumferential rim, the volume equal to at least 5% of a total volume of all solid elements of the lens implant, excluding empty spaces defined by the lens implant.

14. The apparatus according to claim 1, wherein the circumferential rim is attached to the levers such that the entire circumferential rim is farther from the central optical axis than the second longitudinal sites are from the central optical axis.

15. The apparatus according to claim 1, the lens implant is arranged when in the assembled state such that the elastic potential energy stored in the circumferential rim is stored around at least 270 degrees of the circumferential rim.

16. The apparatus according to claim 15, the lens implant is arranged when in the assembled state such that the elastic potential energy stored in the circumferential rim is stored around 360 degrees of the circumferential rim.

17. The apparatus according to claim 1, wherein when the lens implant is in the assembled state:
the posterior lens unit is shaped so as to define one or more ledges that face anteriorly, and
the levers are in the pivotable contact with the one or more ledges at the respective third longitudinal sites along the levers.

18. The apparatus according to claim 17, wherein the circumferential rim is in pivotable contact with the one or more ledges.

19. The apparatus according to claim 17, wherein the posterior lens unit is shaped so as to define a single ledge that extends around an entire circumference of the posterior lens unit.

20. The apparatus according to claim 17, wherein the one or more ledges define one or more respective radially-inward edges, and wherein the levers are in pivotable contact with the one or more radially-inward edges at the respective third longitudinal sites along the levers when the lens implant is in the assembled state.

21. The apparatus according to claim 17, wherein the posterior lens unit is shaped so as to define a circumferential lip that extends anteriorly beyond the one or more ledges, and wherein the one or more ledges project from the circumferential lip radially inward toward the central optical axis.

22. An apparatus comprising an accommodating intraocular lens implant, which is shaped so as to be assemblable into an assembled state in situ in a capsular bag of a human eye so as to have a central optical axis, and which comprises:
an anterior floating lens unit, which comprises an anterior lens;
a posterior lens unit, which comprises a posterior lens;
an anterior rim;
levers, which are, when the lens implant is in the assembled state, (a) (i) in pivotable contact with the anterior floating lens unit at respective first longitudinal sites along the levers, (ii) in pivotable contact with the anterior rim at respective second longitudinal sites along the levers, and (iii) in pivotable contact with the posterior lens unit at respective third longitudinal sites along the levers, and (b) arranged to move the anterior floating lens unit toward and away from the anterior rim, in an anterior-posterior direction, wherein, for each respective lever of the levers, the second longitudinal site is farther from the central optical axis than the first longitudinal site is from the central optical axis, and the third longitudinal site is farther from the central optical axis than the second longitudinal site is from the central optical axis; and a circumferential rim, which is attached to the levers such that at least a portion of the circumferential rim is farther from the central optical axis than the second longitudinal sites are from the central optical axis, wherein the lens implant is arranged such that in the assembled state:

elastic potential energy is stored in the lens implant as a result of deformation of the lens implant during a transition from a fully-accommodated state to a fully-unaccommodated state, and at least 50% of the elastic potential energy stored in the lens implant as the result of the deformation is stored in the circumferential rim, and wherein the circumferential rim is arranged in pivotable contact with the posterior lens unit when the lens implant is in the assembled state.

23. The apparatus according to claim 22, wherein the circumferential rim is arranged in non-jointed pivotable contact with the posterior lens unit when the lens implant is in the assembled state.

24. The apparatus according to claim 22, wherein the circumferential rim is arranged in the pivotable contact with the posterior lens unit around an entire circumference of the circumferential rim when the lens implant is in the assembled state.

25. The apparatus according to claim 22, wherein the circumferential rim and the posterior lens unit are not shaped to provide a snapping interface therebetween.

26. The apparatus according to claim 22, wherein the lens implant is arranged when in the assembled state such that less than 10% of the elastic potential energy in aggregate is stored at one or more interfaces between the circumferential rim and the posterior lens unit, and in the posterior lens unit, in aggregate.

27. The apparatus according to claim 22, wherein the lens implant is arranged such that in the assembled state:

a surface defined by the circumferential rim faces at least partially anteriorly when the lens implant is in the fully-accommodated state, and the surface rotates toward the central optical axis during the transition from the fully-accommodated state to the fully-unaccommodated state.

28. The apparatus according to claim 22, wherein the lens implant is arranged when in the assembled state such that at least 70% of the elastic potential energy stored in the lens implant as the result of the deformation is stored in the circumferential rim.

29. The apparatus according to claim 22, wherein the lens implant is arranged when in the assembled state such that less than 10% of the elastic potential energy in aggregate is stored in the levers at the second longitudinal sites, at respective interfaces between the levers and the anterior rim, and in the anterior rim, in aggregate.

30. The apparatus according to claim 22, wherein the levers, when the lens implant is in the assembled state, are in non-jointed pivotable contact with the anterior rim at the respective second longitudinal sites along the levers.

31. An apparatus comprising an accommodating intraocular lens implant, which is shaped so as to be assemblable into an assembled state in situ in a capsular bag of a human eye so as to have a central optical axis, and which comprises:

an anterior floating lens unit, which comprises an anterior lens;

a posterior lens unit, which comprises a posterior lens;

an anterior rim;

levers, which are, when the lens implant is in the assembled state, (a) (i) in pivotable contact with the anterior floating lens unit at respective first longitudinal sites along the levers, (ii) in pivotable contact with the anterior rim at respective second longitudinal sites along the levers, and (iii) in pivotable contact with the posterior lens unit at respective third longitudinal sites along the levers, and (b) arranged to move the anterior floating lens unit toward and away from the anterior rim, in an anterior-posterior direction, wherein, for each respective lever of the levers, the second longitudinal site is farther from the central optical axis than the first longitudinal site is from the central optical axis, and the third longitudinal site is farther from the central optical axis than the second longitudinal site is from the central optical axis; and a circumferential rim, which is attached to the levers such that at least a portion of the circumferential rim is farther from the central optical axis than the second longitudinal sites are from the central optical axis, wherein the lens implant is arranged such that in the assembled state:

elastic potential energy is stored in the lens implant as a result of deformation of the lens implant during an elastic-potential-energy-storage transition from a fully-accommodated state to a fully-unaccommodated state, at least 50% of the elastic potential energy stored in the lens implant as the result of the deformation is stored in the circumferential rim, during the elastic-potential-energy-storage transition from the fully-accommodated state to the fully-unaccommodated state, the circumferential rim rotates about a circumferential axis thereof in a first rotational direction, thereby storing elastic potential energy, and during an elastic-potential-energy-release transition from the fully-unaccommodated state to the fully-accommodated state, the circumferential rim rotates about the circumferential axis in a second rotational direction opposite the first rotational direction, thereby releasing the stored elastic potential energy.

32. The apparatus according to claim 31, wherein the lens implant is arranged when in the assembled state such that at least 70% of the elastic potential energy stored in the lens implant as the result of the deformation is stored in the circumferential rim.

33. The apparatus according to claim 31, wherein the lens implant is arranged when in the assembled state such that less than 10% of the elastic potential energy in aggregate is stored in the levers at the second longitudinal sites, at respective interfaces between the levers and the anterior rim, and in the anterior rim, in aggregate.

34. The apparatus according to claim 31, wherein the levers, when the lens implant is in the assembled state, are in non-jointed pivotable contact with the anterior rim at the respective second longitudinal sites along the levers.

35. An apparatus comprising an accommodating intraocular lens implant, which is shaped so as to be assemblable into an assembled state in situ in a capsular bag of a human eye so as to have a central optical axis, and which comprises:

an anterior floating lens unit, which comprises an anterior lens;

a posterior lens unit, which comprises a posterior lens;

an anterior rim; and levers, which are, when the lens implant is in the assembled state, (a) (i) in pivotable contact with the anterior floating lens unit at respective first longitudinal sites along the levers, (ii) in non-jointed pivotable contact with the anterior rim at respective second longitudinal sites along the levers, and (iii) in pivotable contact with the posterior lens unit at respective third longitudinal sites along the levers, and (b) arranged to move the anterior floating lens unit toward and away from the anterior rim, in an anterior-posterior direction, wherein, for each respective lever of the levers, the second longitudinal site is farther from the central optical axis than the first longitudinal site is from the central optical axis, and the third longitudinal site is farther from the central optical axis than the second longitudinal site is from the central optical axis.

* * * * *